(12) United States Patent
Kovatchev et al.

(10) Patent No.: US 10,332,615 B2
(45) Date of Patent: Jun. 25, 2019

(54) METHOD AND SYSTEM FOR MODEL-BASED TRACKING OF CHANGES IN AVERAGE GLYCEMIA IN DIABETES

(71) Applicant: University of Virginia Patent Foundation, Charlottesville, VA (US)

(72) Inventors: Boris P. Kovatchev, Charlottesville, VA (US); Marc D. Breton, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 606 days.

(21) Appl. No.: 14/769,638

(22) PCT Filed: Feb. 21, 2014

(86) PCT No.: PCT/US2014/017754
§ 371 (c)(1),
(2) Date: Aug. 21, 2015

(87) PCT Pub. No.: WO2014/130841
PCT Pub. Date: Aug. 28, 2014

(65) Prior Publication Data
US 2016/0004813 A1 Jan. 7, 2016

Related U.S. Application Data

(60) Provisional application No. 61/767,451, filed on Feb. 21, 2013.

(51) Int. Cl.
*G01N 33/48* (2006.01)
*G16B 5/00* (2019.01)
(Continued)

(52) U.S. Cl.
CPC ............ *G16B 5/00* (2019.02); *A61B 5/14532* (2013.01); *A61B 5/7267* (2013.01);
(Continued)

(58) Field of Classification Search
None
See application file for complete search history.

(56) References Cited

U.S. PATENT DOCUMENTS

| 2007/0010950 A1 | 1/2007 | Abensour et al. |
| 2009/0171589 A1 | 7/2009 | Kovatchev |

(Continued)

FOREIGN PATENT DOCUMENTS

| RU | 44 042 U1 | 2/2005 |
| RU | 2283495 C2 | 9/2006 |
| WO | 2011/084208 A1 | 7/2011 |

*Primary Examiner* — Larry D Riggs, II
(74) *Attorney, Agent, or Firm* — Vorys, Sater, Seymour and Pease LLP; Vincent M DeLuca; Robert J. Decker

(57) ABSTRACT

A method, system and computer readable medium for tracking changes in average glycemia in diabetes is based on a conceptually new approach to the retrieval of SMBG data. Using the understanding of HbA1c fluctuation as the measurable effect of the action of an underlying dynamical system, SMBG provides occasional glimpses at the state of this system and, using these measurements, the hidden underlying system trajectory can be reconstructed for individual diabetes patients. Using compartmental modeling a new two-step algorithm is provided that includes: (i) real-time estimate of HbA1c from fasting glucose readings, updated with any new incoming fasting SMBG data point (s), and (ii) initialization and calibration of the estimated HbA1c trace with daily SMBG profiles obtained periodically. The estimation of these profiles includes a factorial model capturing daily BG variability within two latent factors.

25 Claims, 9 Drawing Sheets

(51) Int. Cl.
*G01N 33/487* (2006.01)
*A61B 5/00* (2006.01)
*A61B 5/145* (2006.01)
*G16H 50/50* (2018.01)

(52) U.S. Cl.
CPC ....... *G01N 33/48707* (2013.01); *G16H 50/50* (2018.01); *A61B 5/4839* (2013.01); *A61B 2560/0223* (2013.01); *G01N 2800/042* (2013.01)

(56) References Cited

U.S. PATENT DOCUMENTS

| | | |
|---|---|---|
| 2010/0280499 A1 | 11/2010 | Yodfat et al. |
| 2010/0330598 A1 | 12/2010 | Thukral et al. |
| 2011/0174638 A1 | 7/2011 | Katsuki |
| 2012/0095318 A1 | 4/2012 | Galley |

METHOD AND SYSTEM FOR MODEL-BASED TRACKING OF CHANGES IN AVERAGE GLYCEMIA IN DIABETES

PRIORITY

This application claims priority under 35 U.S.C. § 119(e) and PCT Article 8 and Rule 4.10, from U.S. Provisional Application Ser. No. 61/767,451 filed on 21 Feb. 2013, which application is incorporated herein by reference in its entirety.

BACKGROUND OF THE INVENTION

Since the discovery of an "unusual hemoglobin in patients with diabetes," over 40 years ago[1], Hemoglobin A1c (HbA1c) has become the established standard clinical measurement used as a marker for glycemic control. HbA1c is formed when hemoglobin joins with glucose in the blood, resulting in a glycosylated hemoglobin molecule. Due to the fact that red blood cells survive for 8-12 weeks before renewal, a patient's HbA1c reflects the average blood glucose levels over the past 3 months.

The widespread acceptance of this measurement has primarily been driven by two pivotal, large-scale studies in Type 1 (Diabetes Control and Complications Trial; DCCT) and Type 2 (UK Prospective Diabetes Study; UKPDS) diabetes. These prospective, randomized, controlled trials of intensive versus standard glycemic control in patients with relatively recently diagnosed diabetes demonstrated that intensive glucose control, as measured by blood glucose and HbA1c, correlated with a decreased risk of diabetes-related complications[2,3]. The DCCT and UKPDS, along with other clinical studies, also have been used to support the development of hypothetical scenarios and test mathematical calculation models which aim to describe the relationship between HbA1c and blood glucose.

Linear Models for Blood Glucose-HbA1c Relationship

Based on the UKPDS in type 2 diabetes (T2D) patients a linear regression relationship of HbA1c with fasting plasma glucose (FPG) was observed, where FPG=1.28 (HbA1c)−0.66 ($r2=0.59$).[4] Similarly, using data from the DCCT in type 1 diabetes (T1D) patients, Rohlfing et al. analyzed 26,056 values based on 7 mean blood glucose (MPG) measures per day.[5] Using this approach, they established a linear relationship between plasma glucose and HbA1c (MPG (mmol/l)=(1.98× HbA1c)−4.29 or MPG (mg/dl)=(35.6×HbA1c)−77.3; $r=0.82$). This was subsequently used for the American Diabetes Association (ADA) Standards of Medical Care in Diabetes to describe the correlation between HbA1c and mean glucose. However, in the most recent update, it is now considered that this was not optimal, being derived from relatively sparse data (one 7-point profile over 1 day per HbA1c reading) in the primarily Caucasian T1D participants of the DCCT.[6]

More recently, the ADAG Study Group evaluated data from T1D, T2D and Non-Diabetic patients using self-monitored blood glucose (SMBG).[7] The aim was to define a relationship between HbA1c and average glucose (AG) levels and determine whether HbA1c could be expressed and reported as AG in the same units as used in self-monitoring. Approximately 2,700 glucose values were obtained for each subject during 3 months. Linear regression between the HbA1c and AG values provided the closest correlations, allowing for calculation of an estimated average glucose (eAG) for HbA1c values using the formula AG (mg/dl)=28.7*A1c−46.7; $r2=0.84$; $P<0.0001$. Furthermore the authors found that the linear regression equations did not differ significantly across sub-groups based on age, sex, diabetes type, race/ethnicity, or smoking status. This has now been adopted as the current recommended relationship to use according to the ADA 2011 Standards of Medical Care in Diabetes.[6]

Makris, et al have also observed a similar data pattern, with a strong correlation seen between MBG and HbA1c in Type 2 diabetic patients, using the formula MBG (mg/dl)=(34.74*HbA1c)−79.21 or MBG (mmol/l)=1.91*HbA1c−4.36; $r=0.93$. They also found that the linear regression of MBG values vs. HbA1c at 12 weeks was statistically significant; whereas other independent variables of sex, age, body mass index (BMI) and patient status (Type 2 diabetes treated or not) were not.[8] Temsch et al also identified issues with a linear mathematical model developed to calculate HbA1c values based on SMBG and past HbA1c levels (HbA1c=2.6+0.03*G [mg/100 ml] or 2.6+0.54*G [mmol/l]). Overall, the predicted HbA1c values were consistent with measured values and results matched the HbA1c formula in the elevated range. However, the model was found to be too optimistic in the range of better glycemic control. Sub-analysis suggested that bias may have been introduced by use of different glucometers and individual measurement habits.[9]

Factors Influencing the Relationship Between Blood Glucose and HbA1c

A range of factors have been postulated to influence the relationship HbA1c and blood glucose, such as patient's age, body weight (BMI), gender, ethnicity, behavioral characteristics (e.g. time and frequency of blood glucose measurement) and their general status such as duration and type of diabetes, concomitant diseases, etc.[10,11,12,13]. In particular, two critical areas have been identified which appear to have significant impact on this relationship:

1) The time of blood glucose measurement (fasting (FPG), post-prandial etc.) and
2) The frequency and timing of blood glucose measurement.

Whilst postprandial hyperglycemia, like preprandial hyperglycemia, contributes to elevated HbA1c levels, its relative contribution is higher at HbA1c levels that are closer to 7%. However, the major outcome studies such as the DCCT and UKPDS, relied overwhelmingly on pre-prandial SMBG. Analysis of DCCT found that among individual time points, the afternoon and evening prandial glucose (post-lunch, pre-dinner, post-dinner, and bedtime) readings showed higher correlations with HbA1c than the morning time points (pre-breakfast, post-breakfast, and pre-lunch), with the best correlation of HbA1c being the area under the glucose profile.[14] Yamamoto-Honda et al also showed that FPG and 2-h post-breakfast blood glucose (PBBG) levels exhibited a good sensitivity and specificity for predicting a glycemic control, while the FPG and 3-h PBBG levels only exhibited fair sensitivity and specificity for predicting glycemic control.[15] Similarly chronology and frequency of blood glucose measurements also has influence on the relationship between blood glucose and HbA1c. At any given time, a given blood sample contains erythrocytes of varying ages, with different levels of exposure to hyperglycemia. Whilst the older erythrocytes are likely to have more exposure to hyperglycemia, younger erythrocytes are more numerous. Blood glucose levels from the preceding 30 days contribute approximately 50% to HbA1c, whereas those from the period 90-120 days earlier contribute only approximately 10%.[16] Exploiting further the timing of blood glucose measurements, Trevino challenged the linear model approach as fundamentally flawed and had instead pursued weighted average and nonlinear approaches.[17,18,19]

Development of Non-Linear Models for Blood Glucose-HbA1c Relationship

Several nonlinear models have been proposed, which aim to address additional key factors that influence the relationship between blood glucose and HbA1c. Zielke et al proposed that HbA1c values reflect serum glucose levels of the immediate past much better than levels several weeks ago. Using a biomathematical model that takes into account the chemical reactions during HbA1c formation as well as the life cycle of human erythrocytes, they concluded that in order to ensure some degree of reliability of HbA1c measurements, these readings should not be spaced too far apart.[20] Ollerton et al developed an approach to address the relative contribution of fasting and post-prandial glucose levels to the value of HbA1c, using a mathematical model of hemoglobin glycation. They highlighted that this is based on physiologically reasonable assumptions, to derive a compartmental differential equation model for HbA1c dynamics.[21] Other groups have used data from clinical studies (including DCCT) and hypothetical scenarios, to propose models which incorporate the kinetics of HbA1c formation and removal, in order to better describe the relationship between HbA1c and BGC.[22,23] However, while many of these models may possibly be theoretically sound to some extent, none so far have offered a practically-applicable dynamical approach to tracing the fluctuations of HbA1c over time, an approach that could result in application deployed in an SMBG device ensuring sufficient accuracy by sparse (e.g. fasting glucoses and occasional 7 points profiles) BG measurements.

Risk Analysis of Blood Glucose Data

The present inventors' group at the University of Virginia has also worked extensively on developing models of the relationship between SMBG and HbA1c. In an early study in T1D patients, we investigated how well the mean of SMBG data describes the actual mean BG.[24] The linear formula HbA1c=5.21+0.39*BGMM (mean SMBG expressed in mmol/liter) resulted in a correlation of 0.7 between mean SMBG and HbA1c. Later, an updated linear relationship was derived: HbA1c=0.41046*BGMM+4.0775. However, due to a number of factors associated with routine SMBG, only about 50% of the variance of the actual BG was accounted for by mean SMBG. Thus, these findings suggested that mean SMBG was far from an ideal descriptor of actual average glycemia.

To correct for imperfections in SMBG sampling, we have introduced nonlinear corrections for the SMBG-based estimates of HbA1c, which used results from our theory of risk analysis of BG data[25], namely the Low and High BG Indices (LBGI and HBGI). These nonlinear corrections resulted in improved numerical estimation of HbA1c from SMBG data and introduced mean absolute deviation (MAD) and mean absolute relative deviation (MARD) as measures of the accuracy of HbA1c estimation.[26] This simple step was important for the understanding of HbA1c estimation because while correlation alone measures the strength of a linear association, it does not measure any possible offset of the estimates. For example, an estimate having two-fold higher values than actual HbA1c would have perfect correlation with HbA1c.

Further, based on our risk analysis theory, we introduced a method, system, and computer program, which was designed to aid the control in both T1 and T2 diabetic patients, by predicting from SMBG readings the long-term exposure to hyperglycemia, as well as the long-term and short-term risks for severe or moderate hypoglycemia.[27] This approach used the HBGI and the LBGI, and later a new algorithm which derived an average daily risk range (ADRR)—a variability measure computed from routine SMBG data. We found that the ADRR provided a superior balance of sensitivity for predicting both hypoglycemia and hyperglycemia.[28]

Most importantly for this presentation, we have conducted the largest to date study of the effects of offering real-time SMBG-based estimation of HBA1c, LBGI, and ADRR to patients with diabetes in their natural environment. In this study, 120 people with T1D used for 8-9 months a meter and a handheld computer providing these glycemic markers at each SMBG entry. As a result, average glycemic control was significantly improved, the incidence of severe hypoglycemia was reduced, and the patients rated highly the utility of the provided feedback.[29]

SUMMARY OF THE INVENTION

The above study offered empirical evidence supporting the long-standing belief that providing real-time estimates of HbA1c and risk for hypoglycemia has the desired effect of improving glycemic control. Taking this message forward, we now propose a novel and non-obvious model-based approach (method, system and computer readable medium) to, among other things, track changes in average glycemia from SMBG data. Unlike previously introduced models, this technique (method, system, and computer readable medium) allows for:

Simple parameterization of the dynamics of average glycemia and thereby HbA1c, with two parameters that can be individually tuned to the physiology an behavior of each person;

Robust estimation procedure capable of working on sparse readings of fasting BG and occasional (e.g. monthly) 7-point SMBG profiles; and Inherent capability for calibration of the algorithm (e.g., method) using SMBG profiles.

An aspect of an embodiment of the present invention provides a method, system and computer readable medium for tracking changes in average glycemia in diabetes, based on a conceptually new approach (method and technique) to the retrieval of SMBG data. A principal premise of this approach is, among other things, the understanding of HbA1c fluctuation as the measurable effect of the action of an underlying dynamical system. SMBG provides occasional glimpses at the state of this system and, using these measurements, the hidden underlying system trajectory can be reconstructed for each individual.

Using compartmental modeling—a technique well established in diabetes research[35]—we have constructed a new two-step algorithm (and related method, system and computer readable medium) that includes: (i) real-time estimate of HbA1c from fasting glucose readings, updated with any new incoming fasting SMBG data point, and (ii) initialization and calibration of the estimated HbA1c trace with daily SMBG profiles taken approximately every month. The estimation of these 7-point profiles includes another innovative step—a factorial model capturing daily BG variability into two latent factors.

BRIEF DESCRIPTION OF THE DRAWINGS

The new method, system and computer-readable medium will become more understood from the following detail description, together with detailed algorithm (e.g., technique) and data requirements for its implementation in a portable SMBG device or other desired or required systems or devices, in conjunction with the accompanying drawings, wherein.

DETAILED DESCRIPTION OF THE INVENTION

Algorithm Concept: Dynamical Tracking of Changes in Average Glycemia

Conceptually, a non-limiting embodiment of the estimation procedure for the present invention method, system, and computer readable medium proposed in this disclosure works as follows:

Fasting SMBG readings are submitted to a model of HbA1c dynamics, which tracks the fluctuations of average glycemia over time. This model depends on two individually-adjustable parameters, one of which is fixed to a population value as described below, and the other of which is used to provide inherent ability to individualize (calibrate) the dynamics of HbA1c to a particular person at a particular point in time. For simplification of explanation only, in the exemplary implementation the calibration is fixed for all users.

Periodically (e.g. once a month) a daily SMBG profile is submitted to a factorial model, which reconstructs a person's daily glucose variability via two principal factors (components) that are linear combinations with fixed coefficients of the SMBG values recorded during the day. In this implementation we use standard 7-point profiles;

The factors are then used to calibrate the model for peri-prandial (i.e. pre-prandial and post-prandial) BG deviations from fasting. In other words, the amplitude (variability) of glucose fluctuation is captured using the 7-point profile and is used to adjust the dynamical model to better reflect average glycemia.

Finally an infrequent (1-3 times a year) reference HbA1c measurement can be used to calibrate the glycation formula (link between HbA1c and glucose exposure).

Figure 1:
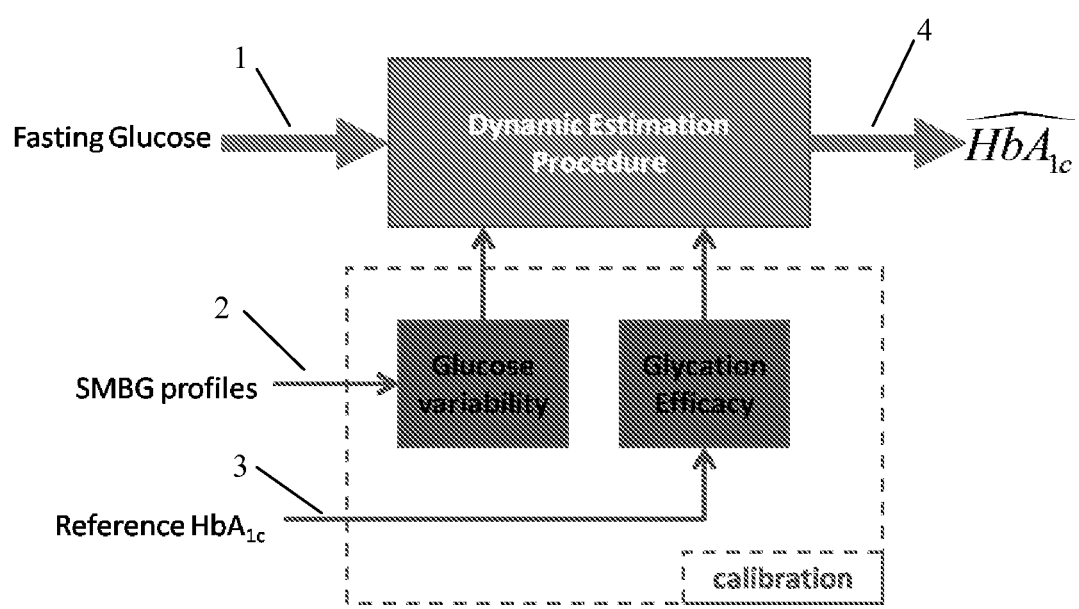
FIG. 1 is a schematic diagram of a system architecture of an HbA1c estimation procedure in accordance with the invention.

FIG. 1 shows a system for the estimation procedure flow. In essence, SMBG measurements are divided in two groups, (i) fasting glucose measurements (1) and (ii) profile glucose measurements (2). Fasting glucose readings are expected once in a couple of days and are the main driving function of the model, while profile measurements are scarce (e.g. monthly) and allow for calibration of the glucose exposure function to the patient's glucose variability. The final result is an estimate of Hba1c (4) that is updated with any incoming fasting SMBG data point (1) and is calibrated with any incoming 7-point profile (2). The SMBG-only system can function as such or be enhanced by reference HbA1c (3) calibration of the calibration formula; in the absence of HbA1c reference (3), the system uses a fixed glycation formula.

Datasets:

The data for training and test data set were provided by Sanofi-Deutschland GmbH originating from the phase IIIb study: Target Glycemic Control and the Incidence of Symptomatic Nocturnal Hypoglycemia in Insulin Naïve Subjects with Type 2 Diabetes on Oral Hypoglycemic Agent(s) and Treated with Insulin Glargine or NPH Human Insulin, HOE901, 4002.

This study was conducted in Type 2 DM patients between 7 Jan. 2000 and 22 Oct. 2001 in 80 study centers in USA and Canada.

The demographics of the ITT study population can be found in Table 1.

Training Data Set:

All formulas were developed using a training data set provided by Sanofi-Aventis Deutschland GmbH, which contained 17,863 fasting SMBG readings and approximately monthly 7-point profiles for 379 individuals with type 2 diabetes (see Table 1 for details.)

On average, each individual contributed 47 days of data. After using the training data, all formulas were fixed and then applied without modification to a test and to an external-validation dataset.

Test data set provided by Sanofi-Aventis Deutschland GmbH was used to validate the formulas developed on the training data. The test data set contained 17,925 fasting SMBG readings and approximately monthly 7-point profiles for 375 individuals with type2 diabetes (see Table 1 for details). On average, each individual contributed 48 days of data.

TABLE 1

Demographics/summary table for training and testing data sets

|  | Female | Men |
|---|---|---|
| Age Average | 54 years | 56 years |
| Age Standard deviation | 9.2 | 9.2 |
| Age Min | 29 years | 30 years |
| Age Max | 74 years | 75 years |
| BMI Average | 33.4 kg/m2 | 31.5 kg/m2 |
| Duration Diabetes | 8.6 years | 8.7 years |
| Height Average | 162.9 cm | 177.3 cm |
| Race | White: 263 | White: 369 |
|  | Black: 59 | Black: 34 |
|  | Multi: 3 | Multi: 6 |
|  | Asian: 10 | Asian: 12 |

TABLE 1-continued

Demographics/summary table for training and testing data sets

|  | Female | Men |
|---|---|---|
| Sex (754 participants) | 44.31% | 55.69% |
| Weight Average | 88.9 kg | 99.5 kg |
| Pregnancy test (712 participants) | Not applicable: 657 Negative: 47 Error Entry: 8 | |
| HbA1c (4351 datapoints) | SD: 1.1 Avg: 7.6% Min: 5.2% Max: 12.2% | |

Figure 2:
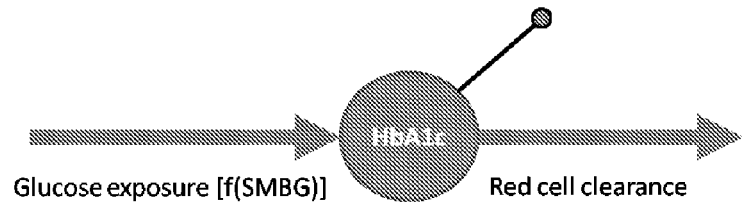
FIG. 2 is a diagram showing a one-compartment model of hemoglobin glycation in accordance with the invention.

Variables:

The variable names were unified across the data sets and are as follows:
SUBNO—subject ID number;
PGDT—time (day) of glucose measurement;
PG1—fasting BG measured pre-breakfast every day;
PG2 to PG8—BG measurements forming a 7-point profile:
PG2: first meal preprandial
PG3: first meal postprandial
PG4: second meal preprandial
PG5: second meal postprandial
PG6: third meal preprandial
PG7: third meal postprandial
PG8: before bedtime Modeling of Fasting BG: Dynamics of HBA1c First, a dynamic model of hemoglobin glycation and clearance is constructed, as shown in FIG. 2. Being mindful that the final goal of the resulting algorithm (method and related system) may be deployment in a portable device with limited computing power, we limit this model to a one-compartment representation.

This model corresponds to a first order differential equation:

$$\frac{\partial \overline{HbA1c}}{\partial t} = -\frac{1}{\tau}(\overline{HbA1c} - f(SMBG_t)) \quad (1)$$

where the function $f(SMBG_t)$ is a function using self-monitoring data to track glycemia exposure over time.

Modeling 7-Point Profiles: Factorial Model of Daily Glucose Variability

Using the training data, a linear model is constructed of the primary factors determining a 7-point profile of SMBG. The reason that we have opted for factors (or principal components) of this profile instead of individual data are the following:
  Statistically, latent factors tend to be more stable and reproducible across diverse data sets;
  Collapsing the entire profile into two factors allows for easy handling of missing data: a missing value in a 7-point profile can be simply imputed in the factorial representation.

With this understanding, the factors are computed as follows:

$$\theta_1 = 0.4006*PG2 + 0.4645*PG3 + 0.3753*PG4 + 0.2411*PG5 - 0.1805*PG6 - 0.2528*PG7 + 0.0481*PG8 \quad (2)$$

$$\theta_2 = -0.1557*PG2 - 0.2077*PG3 - 0.1177*PG4 + 0.0341*PG5 + 0.5255*PG6 + 0.6014*PG7 + 0.2543*PG8 \quad (3)$$

Computational Algorithm:

The implementation of the dynamical model and of factorial models of HbA1c includes initial estimation of Hba1c, tracking of HbA1c fluctuations over time, and occasional (e.g. monthly) calibrations of the tracking value. The initial and the calibration values of HbA1c are obtained using the same formula. The tracking procedure uses the dynamical model of HbA1c setting its parameter values at γ=0.99 and r=20. These two parameters are kept fixed throughout the estimation procedure. The end result is an estimated value of HbA1c, eA1c, given by the formulas below:

Step 1 (optional)—Calibration of HbA1c is derived from the factorial model of 7-point profiles presented in the previous section. Calibration values for HbA1c are computed using the formula:

$$CalA1c = \frac{6.507}{1000}*\theta_1 + \frac{4.353}{1000}*\theta_2 \quad (4)$$

Where: CalA1c is the calibration value for HbA1c derived from the most recent profile;
  $\theta_1$ and $\theta_2$ are the factors defined in the Factorial Model presented above. In the absence of a profile to calibrate, θ1 and θ2 are fixed (e.g. 180).

Step 2—Initial Estimate, and Tracking Changes in Average Glycemia:

The glycation function is given by the formula:

$$f(SMBG_t) = \text{MAX}\left(\gamma*\left(4.7561 + \frac{4.854}{1000}*mP_0(t) + CalA1c\right), 5\right) \quad (5)$$

Where:
  $mP_0(t)$ is the average fasting glucose over the past 5 days and is updated every time a new fasting glucose is measured,
  CalA1c is the calibration offset as computed at the previous step.
  γ is the glycation efficacy parameter and is fixed by default at 0.99 (unless modified by step 3)

Initial Estimate:

To compute an initial estimate (when the device is first used or if a re-initialization is required (see Data Requirements section below) the tracking function is used directly:

$$eA1c(t_0) = f(SMBG_{t_0}) \quad (6)$$

Runtime Estimate

The HbA1c estimate is updated using the dynamic model presented in FIG. 2. For example, the glycation function can be fed into a discretized version (1 day time step) of the dynamic equation above to produce the updated HbA1c estimate eA1c(t): at any time t after initialization of the algorithm:

$$eA1c(t) = 0.95*eA1c(t-1 \text{ day}) + 0.05*f(SMBG_t) \quad (7)$$

In addition, the output of the eA1c algorithm is saturated: instead of providing numerical estimates, values below 6% or above 10% are reported as Low and High respectively. This is done for the following three reasons:
(i) First, clinically, values below 6% are equivalent to values observed in non-diabetics and do not require any action, while values above 10 require significant clinical action regardless of the exact number;
(ii) Second, any estimation procedure would be less robust at the extremes of the HbA1c range and therefore including extreme values would lower unnecessarily its accuracy. This is valid for any estimation, not for this method alone;

(iii) Third, in these data sets, values below 6% and above 10% include less than 5% of all HbA1c records (2.8% below 6 and 1.4% above 10); thus, focusing on the clinically-relevant range of 6-10% HbA1c is also statistically justified.

Step 3 (Optional)—Glycation Formula Calibration:

Equation (5) can be modified using a reference HbA1c calibration:

γ is set in equation (5) so that the eA1c value corresponding to the reference HbA1c measurement. This calibration can occur at anytime in the functioning of the algorithm (e.g., method and related system) but is most efficient after at least a month of data collection.

Results

Figure 3:
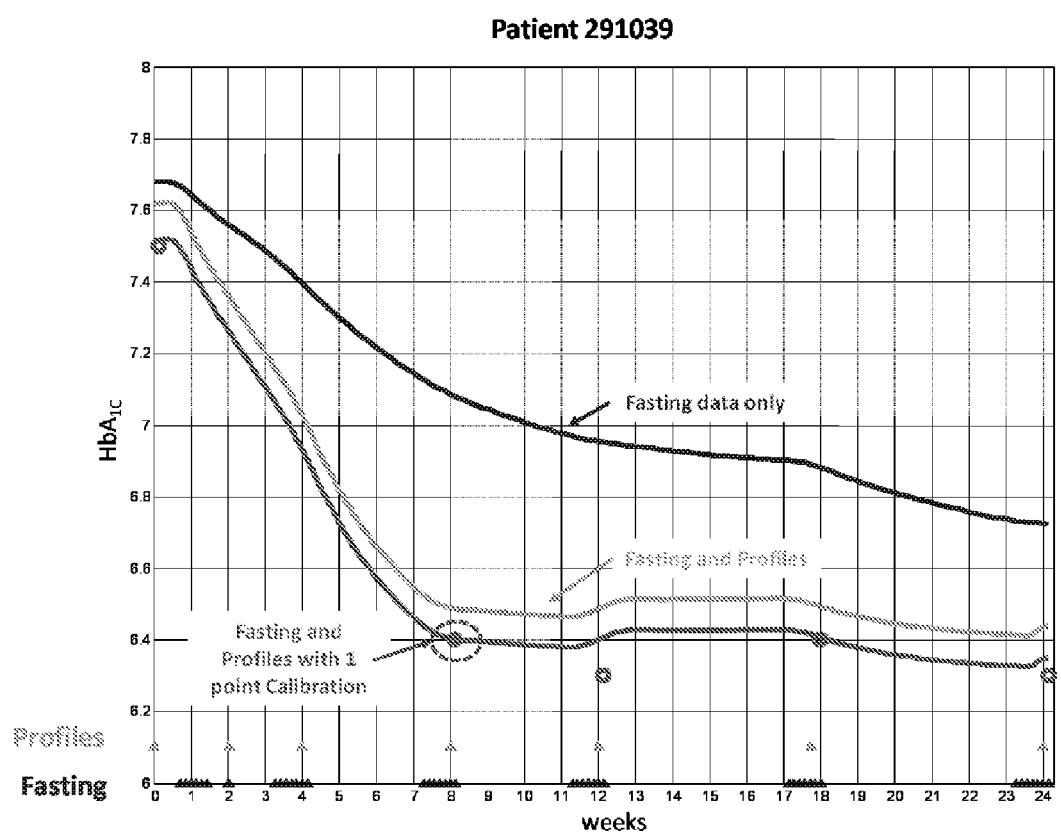
FIG. 3 is a graph of a Dynamical HbA1c Tracking Procedure in accordance with the invention.

An Example: (Patient 291039): FIG. 3 illustrates the procedure tracking changes in average glycemia during normal operation of the method using fasting glucose and 7-point profiles assessed approximately once a month (Fasting and Profiles); with no 7-point profile available (Fasting data only); and enhanced by a 1 point reference HbA1c calibration (Fasting and Profiles with 1 Point Calibration).

Accuracy of the Model-Based eA1c Compared to Model-Free Linear Formula:

In the tables below, the accuracy of estimation of HbA1c (eA1c) using the dynamical method detailed above omitting step 3 (first line of the table) is presented. For comparison with prior established methods, the second line of the table includes the same results for the widely accepted Nathan's linear formula[7] applied on the last 2 weeks of data. In addition to correlations, we use Mean Absolute Deviation (MAD) and Mean Absolute Relative Deviation (MARD) as standard approaches to accuracy evaluation:

TABLE 2

Training data: in the training data set, the method produced the following results:

| Type of Algorithm Operation | Correlation with reference HbA1c | MAD | MARD |
|---|---|---|---|
| eA1c - Dynamic HbA1c Tracking (steps 1-3): tracking fasting glucose; calibration with 7-point profiles approximately once a month and one reference HbA1c | 0.85 | 0.39 | 5.2% |
| eA1c - Dynamic HbA1c Tracking (steps 1-2): tracking fasting glucose; calibration with 7 point profiles approximately once a month | 0.76 | 0.48 | 6.6% |
| Established linear formula (Nathan et al[7]) | 0.73 | 0.96 | 12.8% |

While the table above presents a comparison of our dynamical HbA1c tracking procedure in the training data initially used for algorithm development, the table below presents the same comparisons in a data set that was not used for algorithm development. Thus, Table 3 below should be viewed as the "true test" of algorithm performance as compared to well-established contemporary methods:

TABLE 3

Test data: in the test data set, the method produced the following results:

| Mode of Algorithm Operation | Correlation with reference HbA1c | MAD | MARD |
|---|---|---|---|
| eA1c - Dynamic HbA1c Tracking (steps 1-3): tracking fasting glucose; calibration with 7-point profiles approximately once a month and one reference HbA1c | 0.87 | 0.40 | 5.3% |
| eA1c - Dynamic A1c Tracking (steps 1-2):: tracking fasting glucose; calibration with 7-point profile approximately once a month | 0.76 | 0.51 | 6.8% |
| Established linear formula (Nathan et al[7]) | 0.73 | 0.98 | 13.1% |

It is considered that the most important result above may be MARD—the metric that is typically used to assess accuracy of any direct measurement or other assessment of unknown analyte. Achieving MARD well below 10% signifies that the method is capable of providing accurate and precise tracking of changes in average glycemia over time.

These results indicate that the dynamical estimation procedure proposed herein produces substantially more accurate estimates of HbA1c than the latest widely accepted linear methods. Better accuracy is evident in all data sets used for the testing of the procedure.

Using the dynamical eA1c over other established procedures is particularly adapted to sparse data, e.g. where only fasting glucose is available together with occasional 7-point profiles and simple averages are likely to be biased. In this particular situation (which is common in Type 2 diabetes), having an underlying model has clear robustness advantages over a model-free linear procedure, which is heavily influenced by missing data and tends to produce biased results when limited data is available.

Distribution of eA1c Errors and Trends

This section focuses only on the SMBG-only based A1c estimation (steps 1-2)

HbA1c Error-Grid Analysis

Looking at the distribution of estimation error in the test data set (Table 2), we can make the following statements:
more than 95% of eA1c values fall within ±17% of a standard lab reference measurement; corresponding to 95% of the eA1c values within ±1.17 HbA1c units (%) of the laboratory value.
more than 61% of eA1c values fall within ±7% of a standard lab reference measurement; corresponding to 61% of the eA1c values within ±0.52 HbA1c units (%) of the laboratory value.
more than 53% eA1c values fall within ±6% of a standard lab reference measurement.; corresponding to 53% of the eA1c values within ±0.44 HbA1c units (%) of the laboratory value.

A detailed look at the accuracy of HbA1c estimation is presented in the following pages, beginning with an error-grid type presentation of eA1c values vs. reference HbA1c. The Hba1c error-grid plot below is inspired by graphical error analyses presented in the past for the assessment of the accuracy of SMBG devices, e.g. Clarke Error-Grid[30] or Parkes (also known as Consensus) Error-. Constructing the HbA1c Error Grid we have relied in our extensive expertise Grid[31] analyses with this type of analyses which includes, but is not limited to, the introduction of the Continuous Error Grid now used for evaluation of the accuracy of continuous glucose monitors[32] and recommended by the Clinical and Laboratory Standardization Institute (CLSI) for this purpose[33].

Following the tradition of these Error-Grid plots, we define A-zone for eA1c accuracy as follows:

eA1c is within 10% from reference HbA1c value, or
Both reference HbA1c and eA1c are below 6% Hba1c, or
Both reference HbA1c and eA1c are above 10% Hba1c.

B-zone is defined as eA1c that is within 20% from reference HbA1c value (note that in the established Clarke and Parkes error-grids, the A-zone is 20%; thus our analysis is substantially more demanding). Typically, A-zone is referred to as "Accurate" while B-Zone is referred to as "Benign errors"[30,31] which are generally acceptable in the evaluation of SMBG devices i.e. the cumulative percentage of A+B zone data pairs is used as a metric of device accuracy. Pairs outside of the A+B zones are generally considered erroneous.

HbA1c Error-Grid Analysis for eA1c in the Test Data Set

Figure 4:
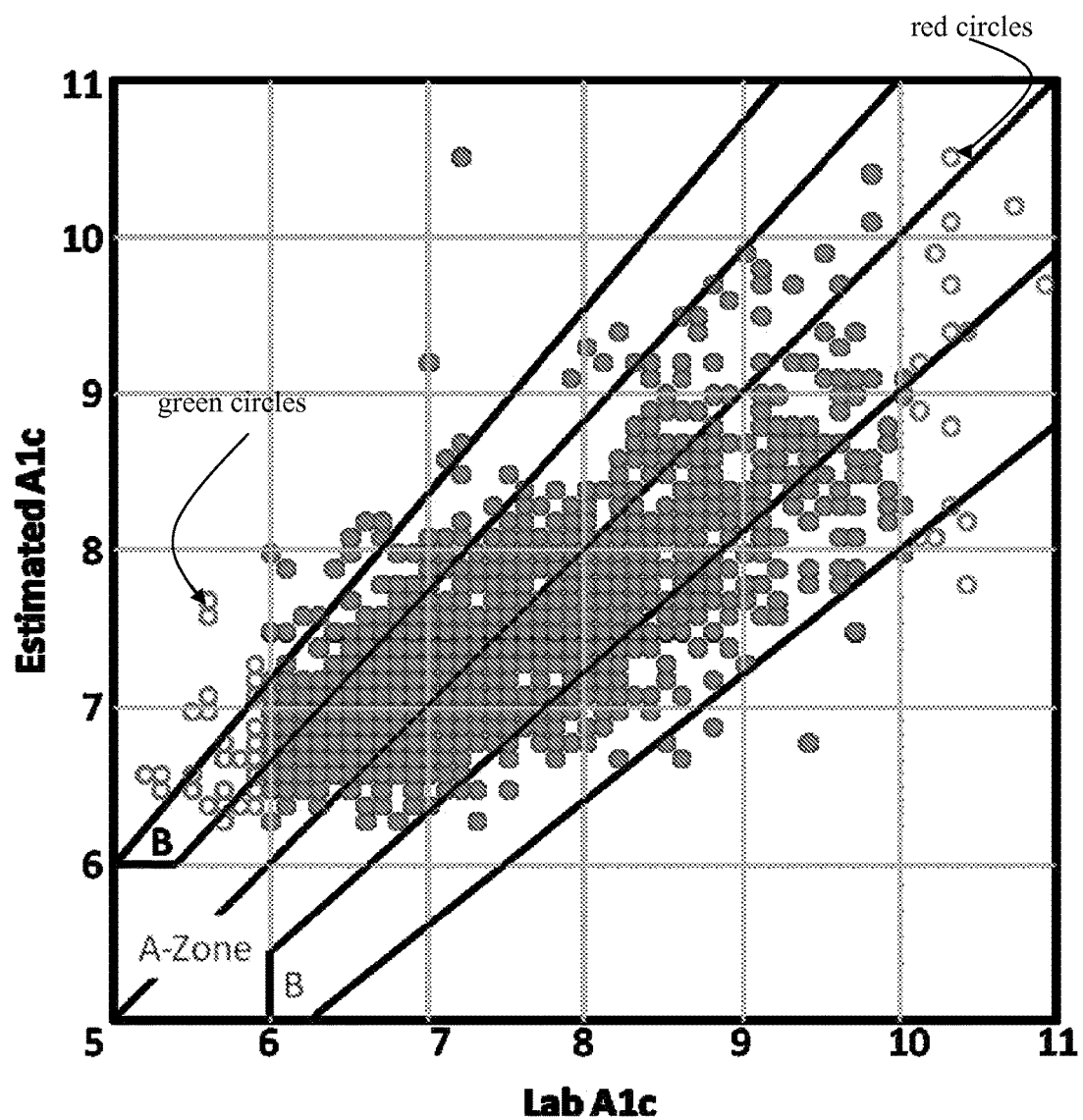
FIG. 4 is a diagram of an HbA1c error-grid for a dynamical HbA1c tracking procedure in accordance with the invention.

With the above in mind, FIG. 4 presents the HbA1c Error-Grid plot for eA1c computed by the formulas above in the Test data set provided by Sanofi-Aventis (Table 2). The data is stratified by reference HbA1c values below 6% (green or hollow circles at the left-hand side of the grid), 6-10% (solid or blue circles) and above 10% (red or hollow circles at the right-hand side of the grid).

In FIG. 4, 76.2% of the all data pairs fall within Zone A of the grid and 97.5% fall within Zones A+B of the grid. If limited to the reportable HbA1c range (6-10%), the accuracy increases to 78.3% A-zone and 98.6% A+B zone, which is comparable to the accuracy of SMBG devices used for BG measurement in the clinical practice. Thus, the estimate of HbA1c derived from SMBG is comparable to the accuracy of the original SMBG readings[34]. This means that the model-based estimation procedure does not introduce further bias in the estimate, beyond the errors inherent with the input SMBG data.

HbA1c Error-Grid Analysis for the Linear Formula in the Test Data Set

Further, to compare the performance of the model-based eA1c to model-free linear estimators of HbA1c we use the same Test data set and plot the HbA1c Error-Grid for the established linear model introduced by Nathan et al[7].

Figure 5:
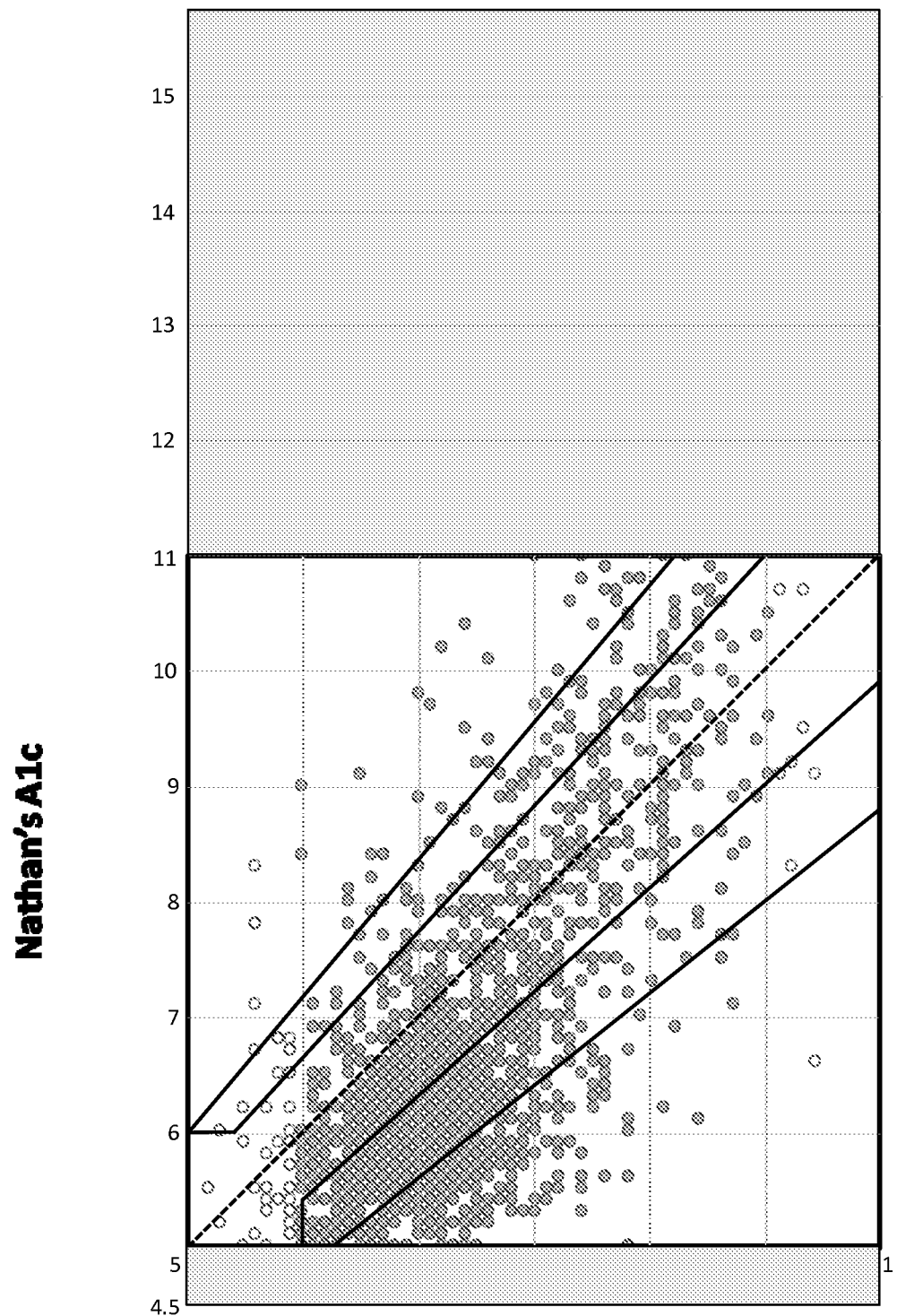
FIG. 5 is a diagram of an HbA1c error-grid for a linear estimate of HbA1c in accordance with the invention.

The grid in FIG. 5 shows that the linear formula tends to overestimate significantly HbA1c, particularly readings above 8% HbA1c, and to underestimate HbA1c readings below 6%. This results in only 43.8% of the all data pairs within.

Zone A of the grid and only 78.6% within Zones A+B of the grid (slightly lower—42.5% and 78%—if the analysis is limited to reference HbA1c of 6-10%). Thus, the linear model has higher error estimating HbA1c than the SMBG data it uses as input. It follows that in this case the linear model tends to amplify the SMBG errors of its input.

The 20-percent difference in A+B zone hits observed between the model-based eA1c and Nathan's linear formula is not only very substantial, but also highlights a basic requirement for any estimation procedure: besides the errors inherent in the data, a good estimator should not introduce additional errors due to the estimation procedure itself.

Distribution of HbA1c Rate of Change

Figure 6:
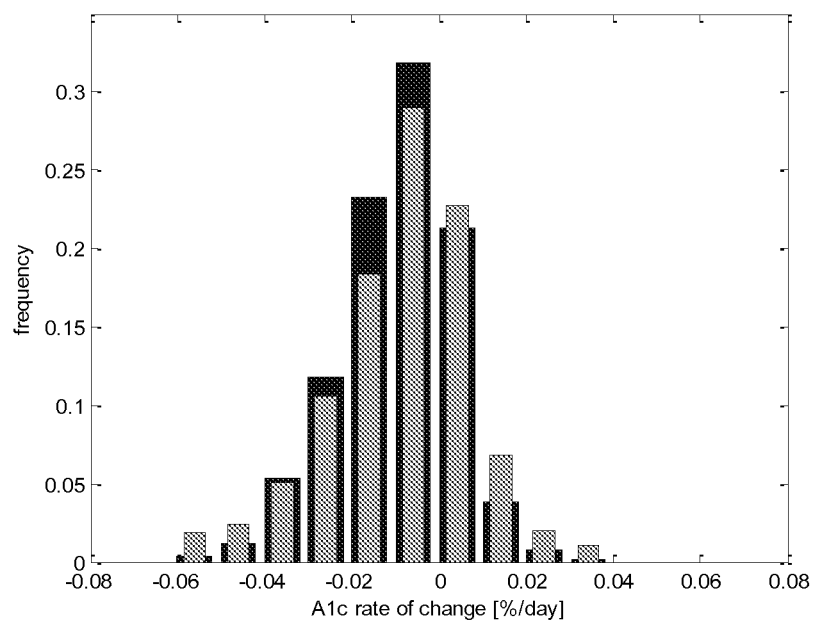
FIG. 6 is a graphical analysis of A1c rate of change in accordance with the invention, wherein the wider bars represent lab values, and the narrow bars represent estimates.

Looking at the distributions of the HbA1c daily rate of change observed in reference HbA1c values and in the dynamical estimate eA1c, we see that these two distributions are very similar (FIG. 6, wide bars for laboratory values). The data shows that there is no difference in the rate of change distributions in laboratory and estimated HbA1c. Thus, accurate trend arrows can be displayed using eA1. The proposed trending system displays down/flat/up arrows, based on the absolute change in eA1c, conditions for arrow display is as follows:

arrow up: eA1c is increasing faster than 0.01% per day (corresponding to an approximately 0.3% eA1c increase in a month);
arrow down: eA1c is decreasing faster than 0.01% per day (corresponding to an approximately 0.3% eA1c decrease in a month);
arrow flat: absolute eA1c changes are less or equal to 0.01% per day.

FIG. 6 is a bar chart showing analysis of the A1c rate of change (wider bars: lab values; narrow bars: estimate).

Robustness Analysis

Stratification of the Estimation Error by Reference HbA1c Levels

By breaking down the accuracy of the HbA1c estimate by HbA1c values, we can determine how precise the eA1c estimate is given a laboratory HbA1c value. We stratify the testing data set by reference HbA1c and observe that the estimation procedure is most accurate in the 7% to 8% range with no bias and 4.5% MARD, which compares favorably to the Nathan's formula[7] (−0.81% bias and MARD 14.4%). Performance degrades on both side of the optimal range. It is to be noted that the eA1c algorithm is designed to not report values below 6% and above 10% (Lo and Hi displays). Within the HbA1c range of 6-10% the bias of eA1c is always less than 1% HbA1c and MARD is below 10%. Complete results are provided in the tables below:

TABLE 4

Bias stratified by laboratory HbA1c levels

|  | HbA1c < 6 | 6 ≤ HbA1c < 7 | 7 ≤ HbA1c < 8 | 8 ≤ HbA1c < 9 | 9 ≤ HbA1c ≤ 10 | HbA1c > 10 |
|---|---|---|---|---|---|---|
| eA1c algorithm | 1.02 n = 40 | 0.49 n = 516 | −0.03 n = 608 | −0.37 n = 265 | −0.83 n = 113 | −1.46 n = 19 |
| Nathan's formula | 0.09 n = 43 | −0.53 n = 518 | −0.81 n = 616 | −0.26 n = 268 | 0.3 n = 115 | 0.53 n = 23 |
|  |  | Reportable HbA1c Range |  |  |  |  |

TABLE 5

MARD stratified by laboratory HbA1c levels

|  | HbA1c < 6 | 6 ≤ HbA1c < 7 | 7 ≤ HbA1c < 8 | 8 ≤ HbA1c < 9 | 9 ≤ HbA1c ≤ 10 | HbA1c > 10 |
|---|---|---|---|---|---|---|
| eA1c algorithm | 17.89<br>n = 40 | 8.01<br>n = 516 | 4.48<br>n = 608 | 6.51<br>n = 265 | 9.49<br>n = 113 | 14.16<br>n = 19 |
| Nathan's formula | 10.81<br>n = 43 | 11.19<br>n = 518 | 14.44<br>n = 616 | 14.19<br>n = 268 | 12.32<br>n = 115 | 15.06<br>n = 23 |
| | | | Reportable HbA1c Range | | | |

Stratification of the Estimation Error by Estimated HbA1c Levels

To answer the question "how much trust should one have, given an eA1c reading?" we offer another type of analysis: stratification of accuracy along estimated, not the reference HbA1c. First note that eA1c should not be used to report any values below 6% or above 10% by design. Within these confines, the eA1c algorithm is very stable, resulting in HbA1c biases between −0.23% and 0.19% and MARDs between 6.74% and 7.24%. In contrast, Nathan's formula shows a clear negative bias at low values and positive bias at high values, likely resulting from heavier weighting of fasting BG in the calculation of the mean. MARD for the Nathan's formula is always higher than for eA1c, with large values (18.3% and 22.5%) at the extremes. In addition, note that the Nathan's formula often predicts low HbA1c (<6%): 527 data points, compared to only 43 true HbA1c values below 6%. Complete results are presented below; see also FIG. 4 and FIG. 5:

TABLE 6

Bias and MARD for eA1c stratified by eA1c levels

|  | eA1c < 6 | 6 ≤ eA1c < 7 | 7 ≤ eA1c < 8 | 8 ≤ eA1c < 9 | 9 ≤ eA1c ≤ 10 | eA1c > 10 |
|---|---|---|---|---|---|---|
| eA1c algorithm | NA<br>n = 0<br>NA<br>n = 0 | 0.11<br>n = 397<br>6.74<br>n = 397 | 0.07<br>n = 870<br>6.80<br>n = 870 | −0.23<br>n = 243<br>6.9<br>n = 243 | 0.19<br>n = 51<br>7.24<br>n = 51 | NA<br>n = 7<br>NA<br>n = 7 |
| | | | Reportable eA1c Range | | | |

TABLE 7

Bias and MARD for Nathan's formula stratified by the levels of Nathan's formula

|  | estimate < 6 | 6 ≤ est. < 7 | 7 ≤ est. < 8 | 8 ≤ est. < 9 | 9 ≤ est. ≤ 10 | est. > 10 |
|---|---|---|---|---|---|---|
| Nathan's formula | −1.29<br>n = 527<br>18.34<br>n = 527 | −0.69<br>n = 497<br>10.27<br>n = 497 | −0.23<br>n = 237<br>7.68<br>n = 237 | 0.19<br>n = 134<br>7.56<br>n = 135 | 0.73<br>n = 95<br>10.95<br>n = 95 | 2.00<br>n = 92<br>22.51<br>n = 92 |
| | | | Reportable eA1c Range | | | |

Analysis of Initial Estimation Errors

To determine if initialization creates larger initial errors compared to overall algorithm functioning, we contrast eA1c performance for the earliest available HbA1c/eA1c pairs for each subject of the testing data set (374 pairs) to the previously reported overall errors.

Table 7 shows that performance in the early phases on eA1c computation is very similar to overall performance. It is to be noted that, due to the progression of the treatment in this study, the first laboratory HbA1c values across the subjects are significantly larger than the subsequent HbA1c values—8.49% vs 7.43%, p<0.01—which explains the slightly larger MAD, while MARD stays stable.

TABLE 8

Performance of eA1c estimation at initialisation vs. overall performance

|  | First pairs | Overall |
|---|---|---|
| MARD | 7.0 | 6.8 |
| MAD | 0.61 | 0.51 |

Sensitivity Analysis

Sensitivity to Missing Fasting Measurements

To perform this analysis we randomly dropped a fixed percentage of fasting BG measurement from the database. The percentage was increased from 0% to 90%. In addition we did not apply the Data Requirements (see below) to explore the limits of the "unprotected" algorithm.

Figure 7:
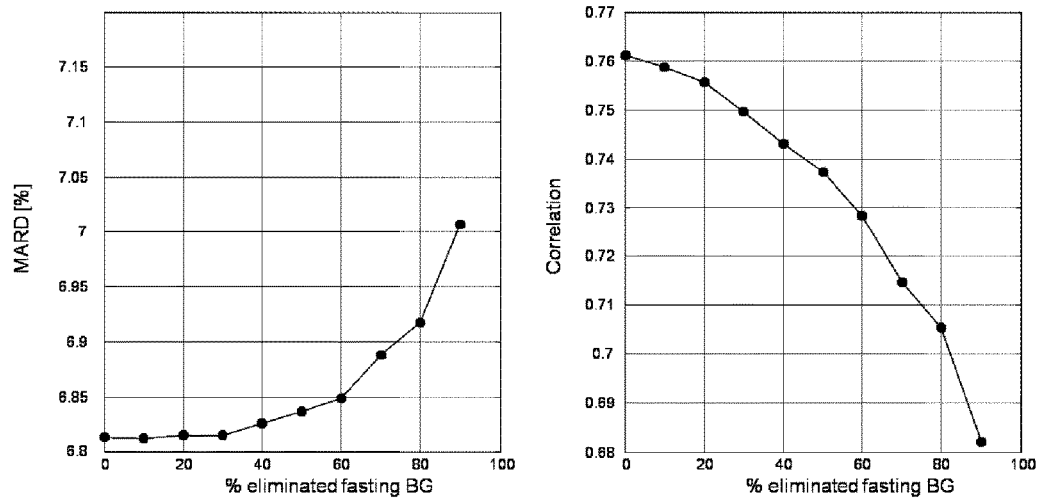
FIG. 7 is a graph showing the effect of missing fasting BG on eA1c estimator performances sensitivity to erroneous profiles in accordance with the invention.

The experiment is repeated 10 times and MARD results are presented in FIG. 7. The eA1c algorithm proves extremely resilient to missing data with overall MARD rising only to 7% from 6.8% when 90% of fasting measurements are eliminated from the data base. Correlation does decrease more rapidly—from 0.76 to 0.68—but remains high.

This analysis assesses degradation in eA1c performance if the user accidentally mixes the tags of a 7 point profiles (e.g. post breakfast is identified as fasting, or post-lunch is confused with pre dinner).

To perform this analysis we randomly identify a fixed percentage of profiles to be scrambled, then for each selected profile we randomly identify 3 pairs of BG measurement (6 values out of the 7 available) and for each pair we transpose the measurements in the profiles. The percentage of scrambled profiles was increased from 0% to 100%.

Figure 8:
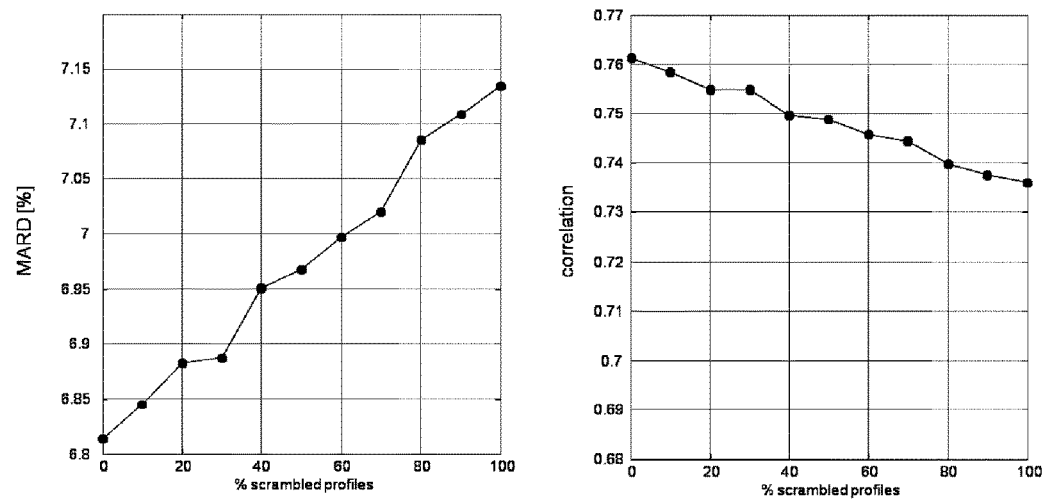
FIG. 8 is a graph showing the effect of scrambled profile tags on eA1c estimator performances sensitivity to alternate site testing (AST) in accordance with the invention.

The experiment is repeated 10 times and MARD results are presented in FIG. 8. Again the eA1c algorithm (and related method, system and computer readable medium) is robust to profile scrambling: MARD rises from 6.81 to 7.14% when all profiles are scrambled, and correlation goes from 0.76 to 0.74. This robustness is attributed to the use of factors (principal components) to quantify the profiles, as discussed above.

Alternate site testing is simulated by adding random noise to each SMBG measurements in the testing data set. The simulated error is normally distributed with zero mean SD=10% (meaning that 95% of the simulated 'AST' measurements are within 20% of the original SMBG value). We repeated the simulation 10 times and for each computed MARD, MAD and correlation between eA1c and lab HbA1c. Results are presented in Table 9. Some of the 10 simulations resulted in marginally degraded performance (far right column in Table 9), but overall the performance using AST was virtually identical to regular SMBG. Again this robustness can be attributed to the use of factors (instead of raw SMBG readings) and to the use of average fasting over 5 days in the tracking formula, which diminished the influence of SMBG errors approximately 2.24-fold (square root of 5).

TABLE 9

Performance of HbA1c estimation using simulated AST glucose measurements

|  | Original analysis | Mean performance across all AST simulations | Worst performance across all AST simulations |
|---|---|---|---|
| MARD | 6.81 | 6.84 | 6.93 |
| MAD | 0.51 | 0.51 | 0.51 |
| Correlation | 0.76 | 0.755 | 0.750 |

Data Requirements

The estimation algorithm (and related method, system and computer readable medium) is built to be robust to missing profiles and occasional missing fasting values. The following minimum requirements and conditions determine when reliable HbA1c estimate can be displayed to the user:

no fasting values for less than 32 days
   A1c estimate cannot be computed or displayed. Estimate will be reinitialized upon fasting BG condition being met again
   user should be advised to measure fasting glucose number of fasting glucose in last 2 weeks is less than 7 or no fasting glucose in the last 5 days
   Estimate is computed but possibly estimate value should not be displayed
   user should be advised to measure fasting glucose time since last profile equal to or is more than 32 days but less than 64 days
   Estimate is computed but possibly estimate value should not be displayed
   user should be advised to provide profiles time since last profile is equal to or more than 64 days or no profile at all
   A1c estimate cannot be computed and displayed. Estimate will be reinitialized upon profile BG condition being met again
   User should be advised to provide profiles time since last profile is less than 32 days, number of fasting glucose in last 2 weeks is greater or equal to 7, and at least one fasting BG in last 5 days
   A1c estimate can be computed and displayed
   user should be encouraged to measure fasting BG daily Summarization and Implementation Examples In diabetes, the struggle for tight glycemic control results in large blood glucose fluctuations over time. This process is influenced by many external factors, including the timing and amount of insulin injected, food eaten, physical activity, etc. In other words, BG fluctuations are the measurable result of the action of a complex dynamical system, influenced by many internal and external factors. The macro (human)-level optimization of this system depends on self-treatment behavior. Thus, such an optimization has to be based on feedback utilizing readily available data, such as SMBG.

Although HbA1c is confirmed as the gold standard marker for average glycemia in both type 1 and type 2 diabetes,[2,3] HbA1c assays typically require a laboratory and are routinely done only every few months. On the other hand, we have shown that providing real-time estimates of HbA1c increases patient motivation and results in improved diabetes control.[29] Thus, tracking of changes in average glycemia is needed that is independent from laboratory HbA1c assays. SMBG offers this possibility, provided that appropriate algorithms (e.g., method, system, and computer readable medium) are employed to retrieve SMBG data.

An aspect of an embodiment of the present invention provides a method, system and computer readable medium for tracking changes in average glycemia in diabetes, based on a conceptually new approach (method and technique) to the retrieval of SMBG data. A principal premise of this approach is, among other things, the understanding of HbA1c fluctuation as the measurable effect of the action of an underlying dynamical system. SMBG provides occasional glimpses at the state of this system and, using these measurements, the hidden underlying system trajectory can be reconstructed for each individual.

Using compartmental modeling—a technique well established in diabetes research[35]—we have constructed a new two-step algorithm (and related method, system and computer readable medium) that includes: (i) real-time estimate of HbA1c from fasting glucose readings, updated with any new incoming fasting SMBG data point, and (ii) initialization and calibration of the estimated HbA1c trace with daily SMBG profiles taken approximately every month. The estimation of these 7-point profiles includes another innovative step—a factorial model capturing daily BG variability into two latent factors.

The development of our method and system followed a robust approach using a training data set to estimate all model parameters. After the initial estimation, all parameters were fixed and the algorithm was run prospectively on an independent test data set. As evident from Tables 1 and 2 above, the results held, which confirms the robustness of the proposed procedure.

Further, we introduce and use HbA1c Error-Grid analysis inspired by the now classic Clarke[30] or Parkes[31] Error-Grids, which permits the graphical representation of accuracy results and the classification of accuracy into A- and B-zones signifying "Accurate" readings or "Benign" errors. This analysis resulted in 98.6% readings in the A+B zones—a result comparable to the accuracy of contemporary SMBG devices[34] (see also FIG. 4).

At every step, we have compared the accuracy of our HbA1c estimator to a well-established linear formula (Nathan et alt), showing that our results are superior according to all analyses. Most striking is the accuracy comparison presented by the HbA1c Error-Grid (FIG. 5), which shows 20% poorer performance by Nathan's formula in the A+B zones. The reason for this difference is in the nature of the data—it is evident that with sparse SMBG readings that include fasting glucose and occasional 7-point profiles, the mean does not represent well the true underlying average of blood glucose fluctuations. As a result, linear formulas based on mean SMBG tend to be significantly biased.

We can therefore conclude that a conceptually new, clinically viable, procedure has been developed for real-time estimation of HBA1c from self-monitoring data. As seen from the algorithm requirements, the procedure is readily applicable into devices, systems and networks with limited processing power, such as for example, but not limited thereto, home SMBG meters.

Figure 9:
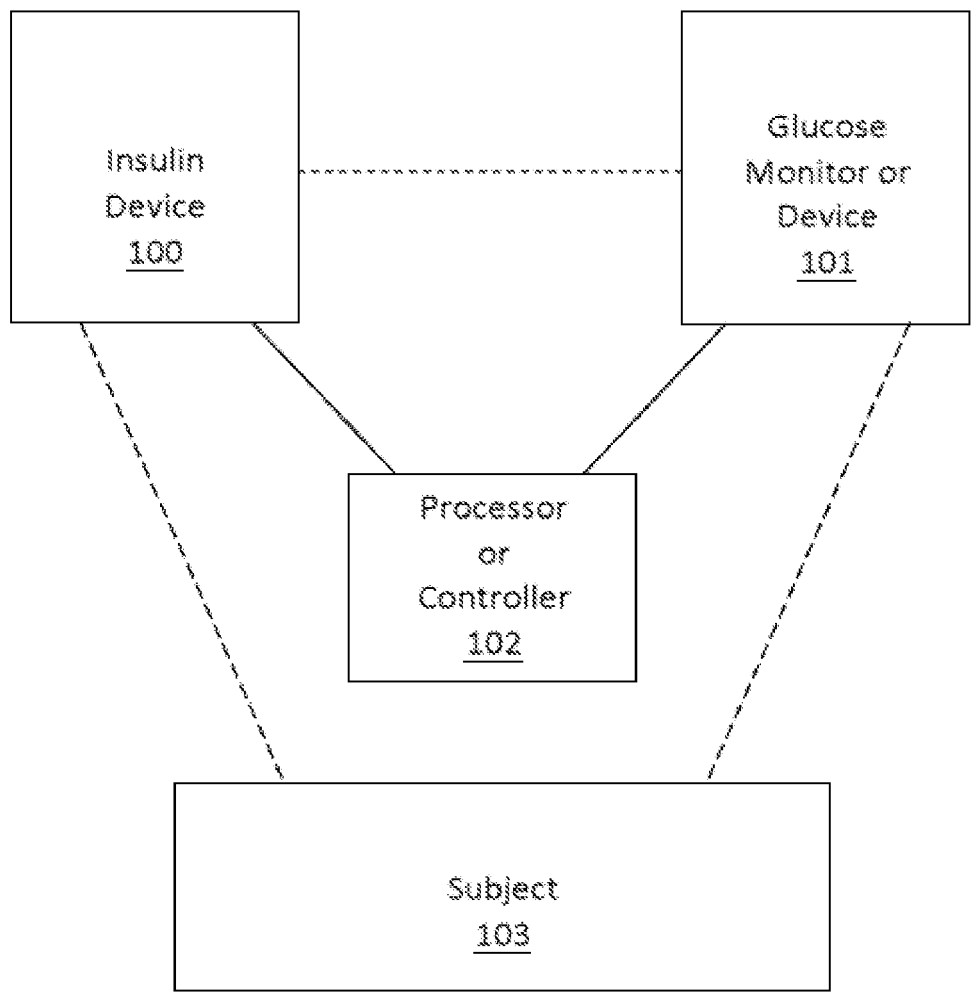
FIG. 9 is a high level functional block diagram of an embodiment of the present invention, or an aspect of an embodiment of the present invention.

Example systems for implementation of the present invention will now be described with reference to FIGS. 9-12. FIG. 9 is a high level functional block diagram of an embodiment of the present invention, or an aspect of an embodiment of the present invention.

As shown in FIG. 9, a processor or controller 102 communicates with the glucose monitor or device 101, and optionally the insulin device 100. The glucose monitor or device 101 communicates with the subject 103 to monitor glucose levels of the subject 103. The processor or controller 102 is configured to perform the required calculations. Optionally, the insulin device 100 communicates with the subject 103 to deliver insulin to the subject 103. The processor or controller 102 is configured to perform the required calculations. The glucose monitor 101 and the insulin device 100 may be implemented as a separate device or as a single device. The processor 102 can be implemented locally in the glucose monitor 101, the insulin device 100, or a standalone device (or in any combination of two or more of the glucose monitor, insulin device, or a stand along device). The processor 102 or a portion of the system can be located remotely such that the device is operated as a telemedicine device.

Figure 10A:
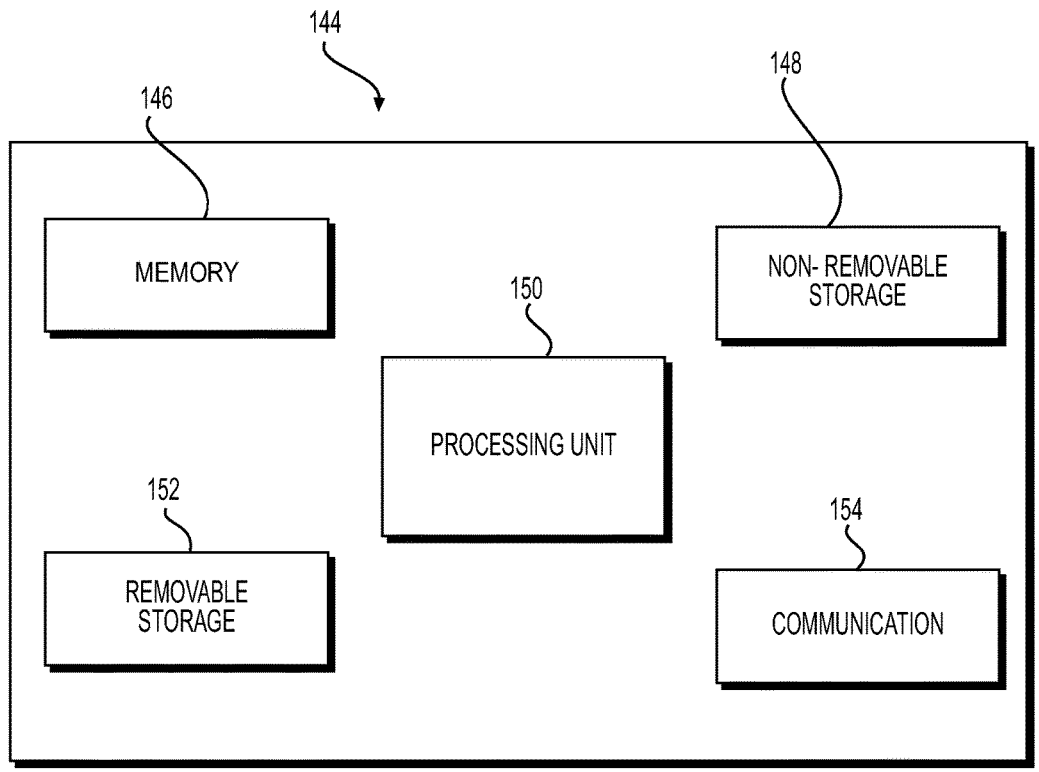
FIG. 10A is a block diagram of a computing device usable with the invention.

Referring to FIG. 10A, in its most basic configuration, computing device 144 typically includes at least one processing unit 150 and memory 146. Depending on the exact configuration and type of computing device, memory 146 can be volatile (such as RAM), non-volatile (such as ROM, flash memory, etc.) or some combination of the two.

Additionally, device 144 may also have other features and/or functionality. For example, the device could also include additional removable and/or non-removable storage including, but not limited to, magnetic or optical disks or tape, as well as writable electrical storage media. Such additional storage is the figure by removable storage 152 and non-removable storage 148. Computer storage media includes volatile and nonvolatile, removable and non-removable media implemented in any method or technology for storage of information such as computer readable instructions, data structures, program modules or other data.

The memory, the removable storage and the non-removable storage are all examples of computer storage media. Computer storage media includes, but is not limited to, RAM, ROM, EEPROM, flash memory or other memory technology CDROM, digital versatile disks (DVD) or other optical storage, magnetic cassettes, magnetic tape, magnetic disk storage or other magnetic storage devices, or any other medium which can be used to store the desired information and which can accessed by the device. Any such computer storage media may be part of, or used in conjunction with, the device. The device may also contain one or more communications connections 154 that allow the device to communicate with other devices (e.g. other computing devices). The communications connections carry information in a communication media. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode, execute, or process information in the signal. By way of example, and not limitation, communication medium includes wired media such as a wired network or direct-wired connection, and wireless media such as radio, RF, infrared and other wireless media. As discussed above, the term computer readable media as used herein includes both storage media and communication media.

Figure 10B:
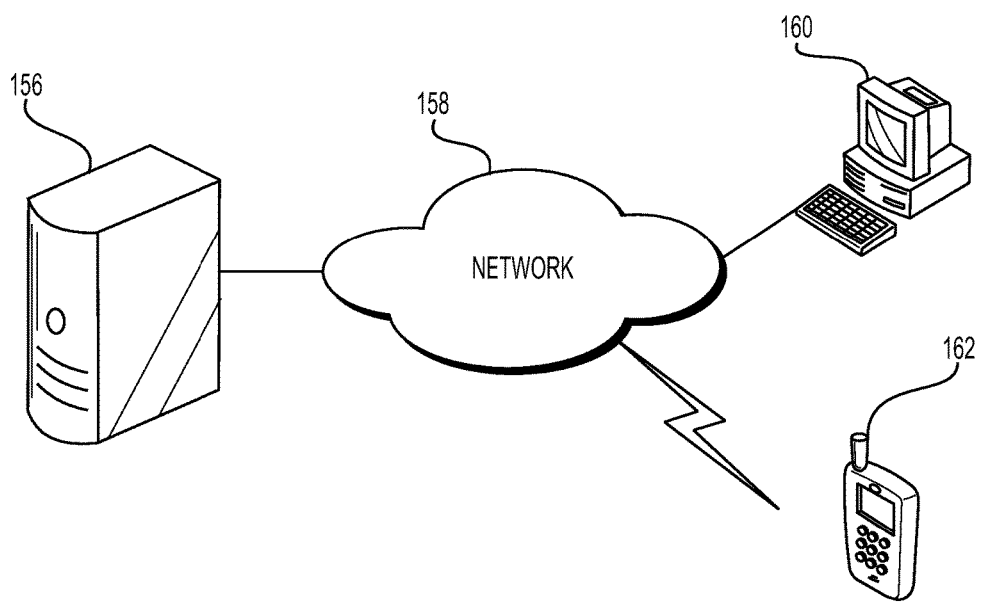
FIG. 10B is a diagram of a network system in which embodiments of the invention can be implemented.

In addition to a stand-alone computing machine, embodiments of the invention can also be implemented on a network system comprising a plurality of computing devices that are in communication with a networking means, such as a network with an infrastructure or an ad hoc network. The network connection can be wired connections or wireless connections. By way of example, FIG. 10B illustrates a network system in which embodiments of the invention can be implemented. In this example, the network system comprises computer 156 (e.g. a network server), network connection means 158 (e.g. wired and/or wireless connections), computer terminal 160, and PDA (e.g. a smart-phone) 162 (or other handheld or portable device, such as a cell phone, laptop computer, tablet computer, GPS receiver, mp3 player, handheld video player, pocket projector, etc. or handheld devices (or non portable devices) with combinations of such features). In an embodiment, it should be appreciated that the module listed as 156 may be glucose monitor device. In an embodiment, it should be appreciated that the module listed as 156 may be a glucose monitor device and/or an insulin device. Any of the components shown or discussed with FIG. 10B may be multiple in number. The embodiments of the invention can be implemented in anyone of the devices of the system. For example, execution of the instructions or other desired processing can be performed on the same computing device that is anyone of 156, 160, and 162. Alternatively, an embodiment of the invention can be performed on different computing devices of the network system. For example, certain desired or required processing or execution can be performed on one of the computing devices of the network (e.g. server 156 and/or glucose monitor device), whereas other processing and execution of the instruction can be performed at another computing device (e.g. terminal 160) of the network system, or vice versa. In fact, certain processing or execution can be performed at one computing device (e.g. server 156 and/or glucose monitor device); and the other processing or execution of the instructions can be performed at different computing devices that may or may not be networked. For example, the certain processing can be performed at terminal 160, while the other processing or instructions are passed to device 162 where the instructions are executed. This scenario may be of particular value especially when the PDA 162 device, for example, accesses to the network through computer terminal 160 (or an access point in an ad hoc network). For another example, software to be protected can be executed, encoded or processed with one or more embodiments of the invention. The processed, encoded or executed software can then be distributed to customers. The distribution can be in a form of storage media (e.g. disk) or electronic copy.

Figure 11:
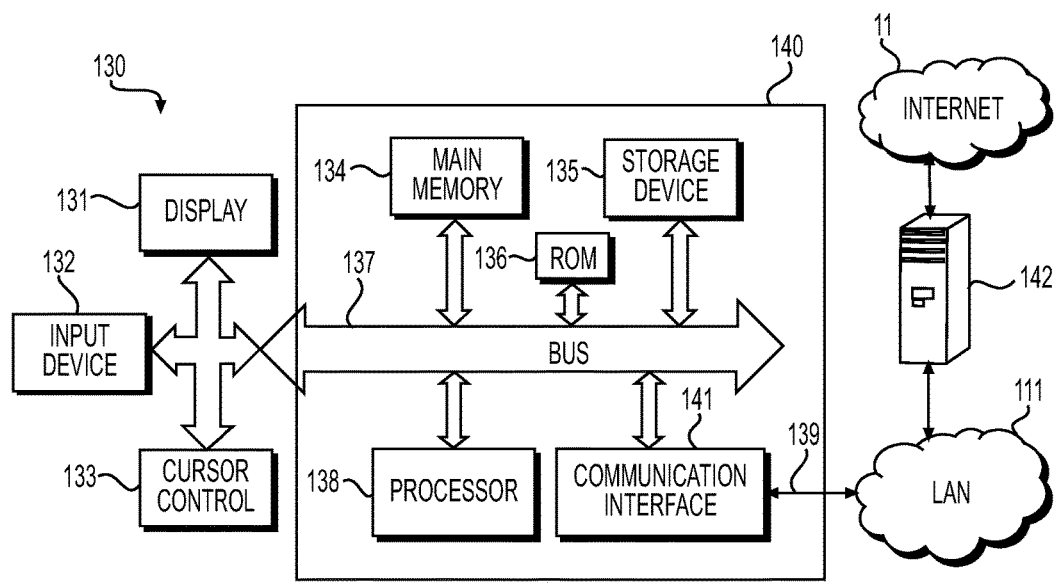
FIG. 11 is a block diagram of a computer system with Internet connectivity, in which an embodiment of the invention may be implemented.

FIG. 11 is a block diagram that illustrates a system 130 including a computer system 140 and the associated Internet 11 connection upon which an embodiment may be implemented. Such configuration is typically used for computers (hosts) connected to the Internet 11 and executing a server or a client (or a combination) software. A source computer such as laptop, an ultimate destination computer and relay servers, for example, as well as any computer or processor described herein, may use the computer system configuration and the Internet connection shown in FIG. 11. The system 140 may be used as a portable electronic device such as a notebook/laptop computer, a media player (e.g., MP3 based or video player), a cellular phone, a Personal Digital Assistant (PDA), a glucose monitor device, an insulin delivery device, an image processing device (e.g., a digital camera or video recorder), and/or any other handheld computing devices, or a combination of any of these devices. Note that while FIG. 11 illustrates various components of a computer system, it is not intended to represent any particular architecture or manner of interconnecting the components; as such details are not germane to the present invention. It will also be appreciated that network computers, handheld computers, cell phones and other data processing systems which have fewer components or perhaps more components may also be used. The computer system of FIG. 11 may, for example, be an Apple Macintosh computer or Power Book, or an IBM compatible PC. Computer system 140 includes a bus 137, an interconnect, or other communication mechanism for communicating information, and a processor 138, commonly in the form of an integrated circuit, coupled with bus 137 for processing information and for executing the computer executable instructions. Computer system 140 also includes a main memory 134, such as a Random Access Memory (RAM) or other dynamic storage device, coupled to bus 137 for storing information and instructions to be executed by processor 138.

Main memory 134 also may be used for storing temporary variables or other intermediate information during execution of instructions to be executed by processor 138. Computer system 140 further includes a Read Only Memory (ROM) 136 (or other non-volatile memory) or other static storage device coupled to bus 137 for storing static information and instructions for processor 138. A storage device 135, such as a magnetic disk or optical disk, a hard disk drive for reading from and writing to a hard disk, a magnetic disk drive for reading from and writing to a magnetic disk, and/or an optical disk drive (such as DVD) for reading from and writing to a removable optical disk, is coupled to bus 137 for storing information and instructions. The hard disk drive, magnetic disk drive, and optical disk drive may be connected to the system bus by a hard disk drive interface, a magnetic disk drive interface, and an optical disk drive interface, respectively. The drives and their associated computer-readable media provide non-volatile storage of computer readable instructions, data structures, program modules and other data for the general purpose computing devices. Typically computer system 140 includes an Operating System (OS) stored in a non-volatile storage for managing the computer resources and provides the applications and programs with an access to the computer resources and interfaces. An operating system commonly processes system data and user input, and responds by allocating and managing tasks and internal system resources, such as controlling and allocating memory, prioritizing system requests, controlling input and output devices, facilitating networking and managing files. Non-limiting examples of operating systems are Microsoft Windows, Mac OS X, and Linux.

The term "processor" is meant to include any integrated circuit or other electronic device (or collection of devices) capable of performing an operation on at least one instruction including, without limitation, Reduced Instruction Set Core (RISC) processors, CISC microprocessors, Microcontroller Units (MCUs), CISC-based Central Processing Units (CPUs), and Digital Signal Processors (DSPs). The hardware of such devices may be integrated onto a single substrate (e.g., silicon "die"), or distributed among two or more substrates. Furthermore, various functional aspects of the processor may be implemented solely as software or firmware associated with the processor.

Computer system 140 may be coupled via bus 137 to a display 131, such as a Cathode Ray Tube (CRT), a Liquid Crystal Display (LCD), a flat screen monitor, a touch screen monitor or similar means for displaying text and graphical data to a user. The display may be connected via a video adapter for supporting the display. The display allows a user to view, enter, and/or edit information that is relevant to the operation of the system. An input device 132, including alphanumeric and other keys, is coupled to bus 137 for communicating information and command selections to processor 138. Another type of user input device is cursor control 133, such as a mouse, a trackball, or cursor direction keys for communicating direction information and command selections to processor 138 and for controlling cursor movement on display 131. This input device typically has two degrees of freedom in two axes, a first axis (e.g., x) and a second axis (e.g., y), that allows the device to specify positions in a plane.

The computer system 140 may be used for implementing the methods and techniques described herein. According to one embodiment, those methods and techniques are performed by computer system 140 in response to processor 138 executing one or more sequences of one or more instructions contained in main memory 134. Such instructions may be read into main memory 134 from another computer-readable medium, such as storage device 135. Execution of the sequences of instructions contained in main memory 134 causes processor 138 to perform the process steps described herein. In alternative embodiments, hard-wired circuitry may be used in place of or in combination with software instructions to implement the arrangement. Thus, embodiments of the invention are not limited to any specific combination of hardware circuitry and software.

The terms "computer-readable medium," "machine-readable medium," or other analogous term as used herein is an extensible term that refers to any medium or any memory, that participates in providing instructions to a processor, (such as processor 138) for execution, or any mechanism for storing or transmitting information in a form readable by a machine (e.g., a computer). Such a medium may store computer-executable instructions to be executed by a processing element and/or control logic, and data which is manipulated by a processing element and/or control logic, and may take many forms, including but not limited to, non-volatile medium, volatile medium, and transmission medium. Transmission media includes coaxial cables, copper wire and fiber optics, including the wires that comprise bus 137. Transmission media can also take the form of acoustic or light waves, such as those generated during radio-wave and infrared data communications, or other form of propagated signals (e.g., carrier waves, infrared signals, digital signals, etc.). Common forms of computer-readable media include, for example, a floppy disk, a flexible disk, hard disk, magnetic tape, or any other magnetic medium, a CD-ROM, any other optical medium, punch-cards, paper-tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to processor 138 for execution. For example, the instructions may initially be carried on a magnetic disk of a remote computer. The remote computer can load the instructions into its dynamic memory and send the instructions over a telephone line using a modem. A modem local to computer system 140 can receive the data on the telephone line and use an infra-red transmitter to convert the data to an infra-red signal. An infra-red detector can receive the data carried in the infra-red signal and appropriate circuitry can place the data on bus 137. Bus 137 carries the data to main memory 134, from which processor 138 retrieves and executes the instructions. The instructions received by main memory 134 may optionally be stored on storage device 135 either before or after execution by processor 138.

Computer system 140 also includes a communication interface 141 coupled to bus 137. Communication interface 141 provides a two-way data communication coupling to a network link 139 that is connected to a local network 111. For example, communication interface 141 may be an Integrated Services Digital Network (ISDN) card or a modem to provide a data communication connection to a corresponding type of telephone line. As another non-limiting example, communication interface 141 may be a local area network (LAN) card to provide a data communication connection to a compatible LAN. For example, Ethernet based connection based on IEEE802.3 standard may be used such as 10/100BaseT, 1000BaseT (gigabit Ethernet), 10 gigabit Ethernet (10 GE or 10 GbE or 10 GigE per IEEE Std 802.3ae-2002 as standard), 40 Gigabit Ethernet (40 GbE), or 100 Gigabit Ethernet (100 GbE as per Ethernet standard IEEE P802.3ba), as described in Cisco Systems, Inc. Publication number 1-587005-001-3 (6/99), "Internetworking Technologies Handbook", Chapter 7: "Ethernet Technologies", pages 7-1 to 7-38, which is incorporated in its entirety for all purposes as if fully set forth herein. In such a case, the communication interface 141 typically include a LAN transceiver or a modem, such as Standard Microsystems Corporation (SMSC) LAN91C111 10/100 Ethernet transceiver described in the Standard Microsystems Corporation (SMSC) data-sheet "LAN91C111 10/100 Non-PCI Ethernet Single Chip MAC+PHY" Data-Sheet, Rev. 15 (Feb. 20, 2004), which is incorporated in its entirety for all purposes as if fully set forth herein.

Wireless links may also be implemented. In any such implementation, communication interface 141 sends and receives electrical, electromagnetic or optical signals that carry digital data streams representing various types of information. Network link 139 typically provides data communication through one or more networks to other data devices. For example, network link 139 may provide a connection through local network 111 to a host computer or to data equipment operated by an Internet Service Provider (ISP) 142. ISP 142 in turn provides data communication services through the world wide packet data communication network Internet 11. Local network 111 and Internet 11 both use electrical, electromagnetic or optical signals that carry digital data streams. The signals through the various networks and the signals on the network link 139 and through the communication interface 141, which carry the digital data to and from computer system 140, are exemplary forms of carrier waves transporting the information.

A received code may be executed by processor 138 as it is received, and/or stored in storage device 135, or other non-volatile storage for later execution. In this manner, computer system 140 may obtain application code in the form of a carrier wave.

The concept of real-time estimation of HbA1c from self-monitoring data has been developed. As seen from the algorithm and methodology requirements discussed herein, the procedure is readily applicable into devices with limited processing power, such as hoe SMBG meters, and may be implemented and utilized with the related processors, networks, computer systems, internet, and components and functions according to the schemes disclosed herein.

Figure 12:
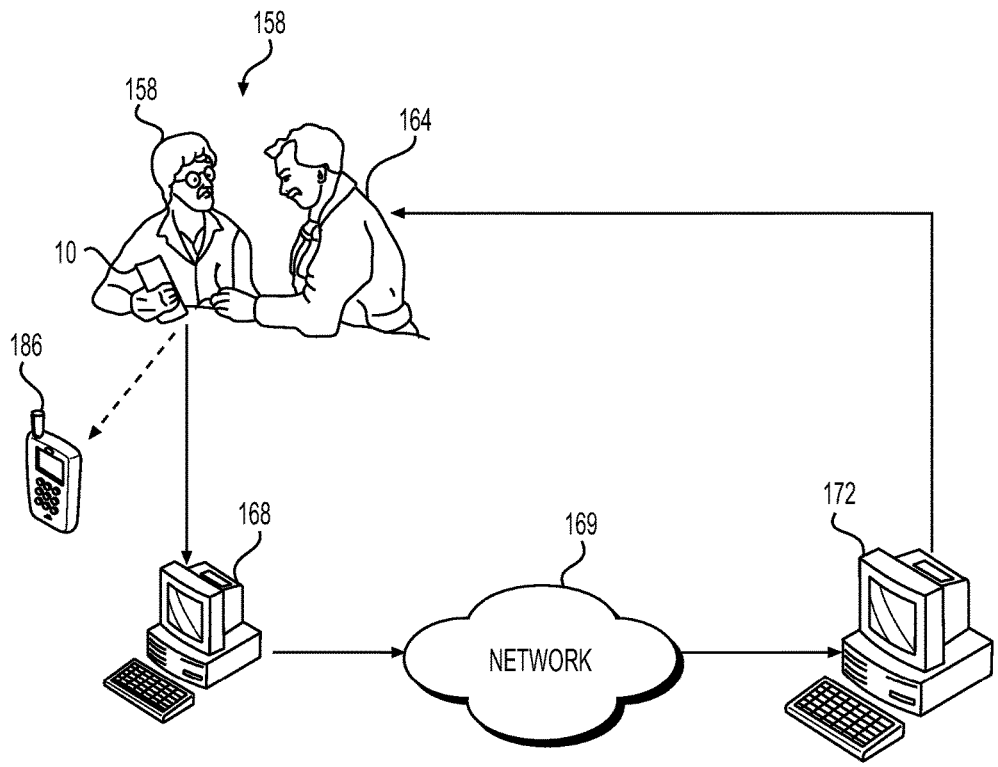
FIG. 12 is a diagram of a system embodiment in accordance with the invention.

FIG. 12 illustrates a system in which one or more embodiments of the invention can be implemented using a network, or portions of a network or computers. Although the present invention glucose device may be practiced without a network.

FIG. 12 diagrammatically illustrates an exemplary system in which examples of the invention can be implemented. In an embodiment the glucose monitor may be implemented by the subject (or patient) locally at home or other desired location. However, in an alternative embodiment it may be implemented in a clinic setting or assistance setting. For instance, referring to FIG. 12, a clinic setup 158 provides a place for doctors (e.g. 164) or clinician/assistant to diagnose patients (e.g. 159) with diseases related with glucose and related diseases and conditions. A glucose monitoring device 10 can be used to monitor and/or test the glucose levels of the patient—as a standalone device. It should be appreciated that while only glucose monitor device 10 is shown in the figure, the system of the invention and any component thereof may be used in the manner depicted by FIG. 12. The system or component may be affixed to the patient or in communication with the patient as desired or required. For example the system or combination of components thereof—including a glucose monitor device 10 (or other related devices or systems such as a controller, and/or an insulin pump, or any other desired or required devices or components)—may be in contact, communication or affixed to the patient through tape or tubing (or other medical instruments or components) or may be in communication through wired or wireless connections. Such monitor and/or test can be short term (e.g. clinical visit) or long term (e.g. clinical stay or family). The glucose monitoring device outputs can be used by the doctor (clinician or assistant) for appropriate actions, such as insulin injection or food feeding for the patient, or other appropriate actions or modeling. Alternatively, the glucose monitoring device output can be delivered to computer terminal 168 for instant or future analyses. The delivery can be through cable or wireless or any other suitable medium. The glucose monitoring device output from the patient can also be delivered to a portable device, such as PDA 166. The glucose monitoring device outputs with improved accuracy can be delivered to a glucose monitoring center 172 for processing and/or analyzing. Such delivery can be accomplished in many ways, such as network connection 170, which can be wired or wireless.

In addition to the glucose monitoring device outputs, errors, parameters for accuracy improvements, and any accuracy related information can be delivered, such as to computer 168, and/or glucose monitoring center 172 for performing error analyses. This can provide a centralized accuracy monitoring, modeling and/or accuracy enhancement for glucose centers, due to the importance of the glucose sensors.

Examples of the invention can also be implemented in a standalone computing device associated with the target glucose monitoring device. An exemplary computing device (or portions thereof) in which examples of the invention can be implemented is schematically illustrated in FIG. 10A.

REFERENCES

The following patents, applications and publications as listed below and throughout this document are hereby incorporated by reference in their entirety herein, and which are not admitted to be prior art with respect to the present invention by inclusion in this section.

1. Rahbar S, Blumenfeld O, Ranney H M. Studies of an unusual hemoglobin in patients with diabetes mellitus. Biochem Biophys Res Commun. 1969; 36: 838-43.
2. The Diabetes Control and Complications Trial Research Group. The effect of intensive treatment of diabetes on the development and progression of long-term complications in insulin-dependent diabetes mellitus. N Engl J Med. 1993; 329: 977-86.
3. UK Prospective Diabetes Study (UKPDS) Group. Intensive blood-glucose control with sulphonylureas or insulin compared with conventional treatment and risk of complications in patients with type 2 diabetes (UKPDS 33). The Lancet. 1998; 352: 837-53.
4. Manley, Susan. Haemoglobin A1c—A marker for complications of type 2 diabetes: The experience from the UK Prospective Diabetes Study (UKPDS), Clinical Chemistry and Laboratory Medicine 2003 41:9 (1182-1190).
5. Rohlfing C L, Wiedmeyer H, Little R R, England J D American Diabetes Association: Diagnosis and Classification of Diabetes Mellitus. Diabetes Care 2010; 33(Suppl. 1): S62-S69.
6. ADA Standards of Care 2011; Diabetes Care, Volume 34, Supplement 1, January 2011, S11-S61.
7. Nathan, D M., Kuenen, J, Borg, R, Zheng, H, Schoenfeld, D, Heine, R J., For The A1c-Derived Average Glucose (ADAG) Study Group. Translating the A1C Assay Into Estimated Average Glucose Values Diabetes Care 31:1473-1478, 2008.
8. Makris, Konstantinos; Spanou, L.; Rambaouni-Antoneli, A.; Koniari, Katerina; Drakopoulos, loannis; Rizos, Demetrios A.; Haliassos, Alexander. Relationship between mean blood glucose and glycated hemoglobin in Type 2 diabetic patients Diabetic Medicine 2008 25:2 (174-178).
9. Temsch, Wilhelm; Luger, Anton F.; Riedl, Michaela. HbA1c values calculated from blood glucose levels using truncated Fourier series and implementation in standard SQL database language. Methods of Information in Medicine 2008 47:4 (346-355).
10. Polneau, S. V.; Lasserre, V.; Fonfrède, M.; Delattre, J.; Bénazeth, S. A different approach to analyzing age-related HbA1c values in non-diabetic subjects. Clinical Chemistry and Laboratory Medicine 2004 42:4 (423-428).
11. Nowicka, Paulina; Santoro, Nicola; Liu, Haibei; Lartaud, Derek; Shaw, Melissa M.; Goldberg, Rachel; Guandalini, Cindy; Savoye, Mary; Rose, Paulina; Caprio, Sonia. Utility of hemoglobin A1c for diagnosing prediabetes and diabetes in obese Children and adolescents. Diabetes Care 2011 34:6 (1306-1311).
12. Hamrén, Bengt; Björk, E.; Sunzel, M.; Karlsson, Mats O. Models for plasma glucose, HbA1c, and hemoglobin interrelationships in patients with type 2 diabetes following tesaglitazar treatment. Clinical Pharmacology and Therapeutics 2008 84:2 (228-235).
13. Heisler, Michele M.; Piette, John D.; Spencer, Michael S.; Kieffer, Edie; Vijan, Sandeep. The relationship between knowledge of recent HbA1c values and diabetes care understanding and self-management. Diabetes Care 2005 28:4 (816-822).
14. Landgraf, Rüdiger. The relationship of postprandial glucose to HbA1c. Diabetes Metab Res Rev 2004 20:SUPPL 2 (S9-S12).
15. Yamamoto-Honda, Ritsuko; Kitazato, Hiroji; Hashimoto, Shinij; Takahashi, Yoshihiko; Yoshida, Yoko; Hasegawa, Chiyoko; Akanuma, Yasuo; Noda, Mitsuhiko. Distribution of blood glucose and the correlation between blood glucose and hemoglobin A1c levels in diabetic outpatients. Endocrine Journal 2008 55:5 (913-923).
16. Goldstein D E, Little R R, Lorenz R A et al. Tests of glycemia in diabetes. Diabetes Care. 2004; 27: 1761-73.
17. Trevino, G. On A1c and its dependence on PG level. Diabetes Research and Clinical Practice 2006 73:1 (111-112).
18. Trevino, G. On the weighted-average relationship between plasma glucose and HbA1c. Diabetes Care 2006 18:2 (466-467).
19. Trevino, G. A nonlinear relation between glucose and A1c. Diabetes Research and Clinical Practice 2008 79:3 (e14).
20. Zielke, Roland; Henrichs, H. R. Use of the HbA1c determination as long-term parameter in diabetes control. Klinisches Labor 1993 39:12 (988-990).
21. Ollerton, R. L.; Luzio, S. D.; Owens, D. R. Contribution of fasting and postprandial plasma glucose to HbA(1c) Diabetic Medicine 2005 22:7 (954-955).
22. Osterman-Golkar, S. M.; Vesper, H. W. Assessment of the relationship between glucose and A1c using kinetic modelling. Journal of Diabetes and its Complications 2006 20:5 (285-294).
23. Kahrom, M. An innovative mathematical model: A key to the riddle of HbA1c. International Journal of Endocrinology 2010 Article Number 481326.
24. Kovatchev, B. P.; Cox, D. J.; Straume, M.; Farhy, L. S. Association of self-monitoring blood glucose profiles with glycolysated hemoglobin in patients with insulin-dependent diabetes. Methods in Enzymology 2000 321 (410-417)
25. Kovatchev B P, Straume M, Cox D J, Farhy L S. Risk analysis of blood glucose data: A quantitative approach to optimizing the control of insulin dependent diabetes. *J of Theoretical Medicine,* 3:1-10, 2001.
26. Kovatchev B P, Cox D J. Numerical Estimation of $HbA_{1c}$ from Routine Self-Monitoring Data in People With Type 1 and Type 2 Diabetes Mellitus (2004). In: *Methods in Enzymology,* 384: *Numerical Computer Methods, Part E:* 94-106. M Johnson and L Brand, Eds., Academic Press, NY. ISBN: 978-0-12-182789-2.

27. Kovatchev B P, Cox D J, Kumar A, Gonder-Frederick L A, Clarke W L (2003). Algorithmic Evaluation of Metabolic Control and Risk of Severe Hypoglycemia in Type 1 and Type 2 Diabetes Using Self-Monitoring Blood Glucose (SMBG) Data. Diabetes Technology and Therapeutics, 5 (5): 817-828.
28. Kovatchev B P, Otto E, Cox D, Gonder-Frederick L, Clarke W. Evaluation of a new measure of blood glucose variability in diabetes. Diabetes Care. 2006 November; 29 (11): 2433-8.
29. Kovatchev B P, Mendosa P, Anderson S, Hawley J S, Ritterband L M, Gonder-Frederick L. Effect of automated bio-behavioral feedback on the control of type 1 diabetes. Diabetes Care. 2011 February; 34 (2):302-7. Epub 2011 Jan. 7.
30. Clarke W L, Cox D, Gonder-Frederick L A, Carter W, Pohl S L. Evaluating clinical accuracy of systems for self-monitoring of blood glucose. Diabetes Care. 1987; 10(5):622-8.
31. Parkes J L, Slatin S L, Pardo S, Ginsberg B H. A new consensus error grid to evaluate the clinical significance of inaccuracies in the measurement of blood glucose. Diabetes Care. 2000; 23(8):1143-8.
32. Kovatchev B P, Gonder-Frederick L A, Cox D J, Clarke W L. Evaluating the accuracy of continuous glucose-monitoring sensors: continuous glucose-error grid analysis illustrated by TheraSense Freestyle Navigator data. Diabetes Care. 2004; 27:1922-8.
33. Clinical and Laboratory Standards Institute (CLSI). Performance Metrics for Continuous Interstitial Glucose Monitoring: Approved Guideline. CLSI document, POCT-A, 2008.
34. Boren S A, Clarke W L. Analytical and clinical performance of blood glucose monitors. *J Diabetes Sci Technol.* 2010; 4(1):84-97.
35. Cobelli C, Dalla Man C, Sparacino G, Magni L, Nicolao G, and Kovatchev B P (2009). Diabetes: Models, Signals, and Control. IEEE Reviews in Biomedical Engineering, 2: 54-96.

The devices, systems, computer readable medium, algorithms, models, and methods of various embodiments of the invention disclosed herein may utilize aspects disclosed in the following references, applications, publications and patents and which are hereby incorporated by reference herein in their entirety (and which are not admitted to be prior art with respect to the present invention by inclusion in this section):

A. U.S. patent application Ser. No. 13/637,359, entitled "Method, System, and Computer Program Product for Improving the Accuracy of Glucose Sensors Using Insulin Delivery Observation in Diabetes", filed Sep. 25, 2012;
B. U.S. patent application Ser. No. 13/634,040, entitled "Method and System for the Safety, Analysis, and Supervision of Insulin Pump Action and Other Modes of Insulin Delivery in Diabetes", filed Sep. 11, 2012.
C. International Patent Application Serial No. PCT/US2012/052422, entitled "Method, System and Computer Readable Medium for Adaptive Advisory Control of Diabetes", filed Aug. 26, 2012;
D. International Patent Application Serial No. PCT/US2012/043910, entitled "Unified Platform For Monitoring and Control of Blood Glucose Levels in Diabetic Patients" filed Jun. 23, 2012;
E. International Patent Application Serial No. PCT/US2012/043883, entitled "Methods and Apparatus for Modular Power Management and Protection of Critical Services in Ambulatory Medical Devices", filed Jun. 22, 2012;
F. U.S. patent application Ser. No. 13/394,091, entitled "Tracking the Probability for Imminent Hypoglycemia in Diabetes from Self-Monitoring Blood Glucose (SMBG) Data filed Mar. 2, 2012;
G. U.S. patent application Ser. No. 13/393,647 filed Mar. 1, 2012, National Stage of PCT/US2010/047386, entitled "System, Method and Computer Program Product for Adjustment of Insulin Delivery (AID) in Diabetes Using Nominal Open-Loop Profiles" filed Aug. 31, 2010;
H. U.S. patent application Ser. No. 13/380,839 filed Feb. 10, 2012, National Stage of PCT/US2010/040097, entitled "System, Method and Computer Stimulation Environment for In Silico Trials in Prediabetes and Type 2 Diabetes" filed Jun. 25, 2010;
I. International Patent Application Serial No. PCT/US2011/029793, entitled "Method, System and Computer Program Product for Improving the Accuracy of Continuous Glucose Sensors Using Insulin Delivery Observation in Diabetes" filed Mar. 24, 2011;
J. International Patent Application Serial No. PCT/US2011/028163, entitled "Method and System for the Safety, Analysis, and Supervision of Insulin Pump Action and Other Modes of Insulin Delivery in Diabetes" filed Mar. 11, 2011;
K. U.S. patent application Ser. No. 12/975,580, entitled "System, Method and Computer Program Product for Adjustment of Insulin Delivery (AID) in Diabetes Using Nominal Open-Loop Profiles", filed Dec. 22, 2010;
L. International Patent Application Serial No. PCT/US2010/047711, entitled "Tracking the Probability for Hypoglycemia in Diabetes from Self-Monitoring Blood Glucose (SMBG) Data, filed Sep. 2, 2010;
M. International Patent Application Serial No. PCT/US2010/047386, entitled "System Coordinator and Modular Architecture for Open-Loop and Closed-Loop Control of Diabetes", Aug. 31, 2010;
N. International Patent Application Serial No. PCT/US2010/036629, entitled "System Coordinator and Modular Architecture for Open-Loop and Closed-Loop Control of Diabetes", filed May 28, 2010;
O. International Patent Application Serial No. PCT/US2010/025405, entitled "Method, System and Computer Program Product for CGM-Based Prevention of Hypoglycemia via Hypoglycemia Risk Assessment and Smooth Reduction Insulin Delivery," filed Feb. 25, 2010;
P. International Patent Application Serial No. PCT/US2009/065725, entitled "Method, System, and Computer Program Product for Tracking of Blood Glucose Variability in Diabetes from Data," filed Nov. 24, 2009;
Q. International Patent Application Serial No. PCT/US2008/082063, entitled "Model Predictive Control Based Method for Closed-Loop Control of Insulin Delivery in Diabetes Using Continuous Glucose Sensing", filed Oct. 31, 2008;
R. PCT/US2008/069416, entitled "Method, System and Computer Program Product for Evaluation of Insulin Sensitivity, Insulin/Carbohydrate Ratio, and Insulin Correction Factors in Diabetes from Self-Monitoring Data", filed Jul. 8, 2008;
S. PCT/US2008/067725, entitled "Method, System and Computer Simulation Environment for Testing of Monitoring and Control Strategies in Diabetes," filed Jun. 20, 2008;
T. PCT/US2008/067723, entitled "LQG Artificial Pancreas Control System and Related Method", filed on Jun. 20, 2008;

U. U.S. patent application Ser. No. 12/516,044, entitled "Method, System, and Computer Program Product for the Detection of Physical Activity by Changes in Heart Rate, Assessment of Fast Changing Metabolic States, and Applications of Closed and Open Control Loop in Diabetes", filed May 22, 2009;

V. PCT/US2007/085588, entitled "Method, System, and Computer Program Product for the Detection of Physical Activity by Changes in Heart Rate, Assessment of Fast Changing Metabolic States, and Applications of Closed and Open Control Loop in Diabetes", filed Nov. 27, 2007;

W. U.S. Ser. No. 11/943,226, entitled "Systems, Methods and Computer Program Codes for Recognition of Patterns of Hyperglycemia and Hypoglycemia, Increased Glucose Variability, and Ineffective Self-Monitoring in Diabetes" filed Nov. 20, 2007;

X. U.S. patent application Ser. No. 11/578,831, entitled "Method, System and Computer Program Product for Evaluating the Accuracy of Blood Glucose Monitoring Sensors/Devices", filed Oct. 18, 2006;

Y. PCT International Application Serial No. PCT/US2005/013792, entitled "Method, System, and Computer Program Product for Evaluation of the Accuracy of Blood Glucose Monitoring Sensors/Devices", filed Apr. 21, 2005;

Z. PCT International Application Serial No. PCT/US01/09884, entitled "Method, System, and Computer Program Product for Evaluation of Glycemic Control in Diabetes Self-Monitoring Data", filed Mar. 29, 2001;

AA. U.S. Pat. No. 7,025,425 B2 issued Apr. 11, 2006, entitled "Method, System, and Computer Program Product for the Evaluation of Glycemic Control in Diabetes from Self-Monitoring Data";

BB. U.S. patent application Ser. No. 11/305,946 filed Dec. 19, 2005 entitled "Method, System, and Computer Program Product for the Evaluation of Glycemic Control in Diabetes from Self-Monitoring Data" (Publication No. 2006/0094947);

CC. PCT International Application Serial No. PCT/US2003/025053, filed Aug. 8, 2003, entitled "Method, System, and Computer Program Product for the Processing of Self-Monitoring Blood Glucose (SMBG) Data to Enhance Diabetic Self-Management;"

DD. U.S. patent application Ser. No. 10/524,094 filed Feb. 9, 2005 entitled "Managing and Processing Self-Monitoring Blood Glucose" (Publication No. 2005/214892);

EE. U.S. Ser. No. 12/065,257, filed Aug. 29, 2008, entitled "Accuracy of Continuous Glucose Sensors;"

FF. PCT International Application Serial No PCT/US2006/033724, filed Aug. 29, 2006, entitled "Method for Improvising Accuracy of Continuous Glucose Sensors and a Continuous Glucose Sensor Using the Same";

GG. U.S. Ser. No. 12/159,891, filed Jul. 2, 2008, entitled "Method, System and Computer Program Product for Evaluation of Blood Glucose Variability in Diabetes from Self-Monitoring Data";

HH. PCT International Application No. PCT/US2007/000370, filed Jan. 5, 2007, entitled "Method, System and Computer Program Product for Evaluation of Blood Glucose Variability in Diabetes from Self-Monitoring Data";

II. U.S. patent application Ser. No. 11/925,689 and PCT International Patent Application No. PCT/US2007/082744, both filed Oct. 26, 2007, entitled "For Method, System and Computer Program Product for Real-Time Detection of Sensitivity Decline in Analyte Sensors";

JJ. U.S. Ser. No. 10/069,674, filed Feb. 22, 2002, entitled "Method and Apparatus for Predicting the Risk of Hypoglycemia";

KK. PCT International Application No. PCT/US00/22886, filed Aug. 21, 2000, entitled "Method and Apparatus for Predicting the Risk of Hypoglycemia"; and LL. U.S. Pat. No. 6,923,763 B1, issued Aug. 2, 2005, entitled "Method and Apparatus for Predicting the Risk of Hypoglycemia".

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the following disclosure, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary.

Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

What is claimed is:

1. A computer-implemented method for providing a real-time estimate of glycosylated hemoglobin (HbA1c) of a patient from a self-monitoring blood glucose (SMBG) measurement, and tracking changes in average glycemia of said patient over time, said method comprising:
- receiving, by a processor, a fasting SMBG measurement from said patient;
- computing, by a processor, a glycation value using said fasting SMBG measurement in a predetermined glycation equation;
- outputting, by a processor, said glycation value as an initial estimate of HbA1c upon initialization of tracking of said patient's average glycemia;
- updating, by a processor, said glycation value by using an updated SMBG value in said predetermined glycation equation, said updated SMBG value being based on a subsequent fasting SMBG measurement from said patient;
- computing, by a processor, an updated estimate of HbA1c using said initial estimate of HbA1c and said updated glycation value in a predetermined HbA1c estimation equation; and
- outputting, by a processor, said updated estimate of HbA1c to a user.

2. The computer-implemented method of claim 1, further comprising:
- updating, by a processor, said updated estimate of HbA1c by:
  - using a subsequent updated SMBG value in said predetermined glycation equation based on a further subsequent fasting SMBG measurement from said patient to compute a further updated glycation value; and
  - computing, by a processor, a further updated estimate of HbA1c using a last updated estimate of HbA1c and said further updated glycation value in a predetermined HbA1c estimation equation; and
- outputting, by a processor, said further updated estimate of HbA1c to a user.

3. The computer-implemented method of claim 2, wherein said predetermined glycation equation is given by:

$$f(SMBG_t) = \text{MAX}\left(\gamma * \left(4.7561 + \frac{4.854}{1000} * mP_0(t) + CalA1c\right), 5\right)$$

where
- $mP_0(t)$ is the average fasting glucose over a predetermined period of time and is updated every time a new fasting glucose measurement is obtained from said patient,
- CalA1c is a calibration offset, and
- $\gamma$ is a glycation efficacy parameter;

the initial estimate of HbA1c is given by $eA1c(t_0) = f(SMBG_{t_0})$; and the updated estimate of HbA1c is given by $eA1c(t) = 0.95 * eA1c(t-1 \text{ day}) + 0.05 * f(SMBG_t)$.

4. The computer-implemented method of claim 3, wherein $\gamma$ is set so that the last updated estimate of HbA1c, eA1c(t), is set to correspond to a reference HbA1c measurement obtained from said patient.

5. The computer-implemented method of claim 3, wherein $$CalA1c = \frac{6.507}{1000} * \theta_1 + \frac{4.353}{1000} * \theta_2,$$

$\theta_1$ and $\theta_2$ are predefined factors in a SMBG profile of said patient.

6. The computer-implemented method of claim 5, wherein said SMBG profile is a multipoint peri-prandial profile.

7. The computer-implemented method of claim 6, wherein said multipoint peri-prandial profile is a seven point profile including the following SMBG measurements:
- PG2: first meal preprandial
- PG3: first meal postprandial
- PG4: second meal preprandial
- PG5: second meal postprandial
- PG6: third meal preprandial
- PG7: third meal postprandial
- PG8: before bedtime.

8. The computer-implemented method of claim 7, wherein $\theta_1 = 0.4006*PG2 + 0.4645*PG3 + 0.3753*PG4 + 0.2411*PG5 - 0.1805*PG6 - 0.2528*PG7 + 0.0481*PG8$, and $\theta_2 = -0.1557*PG2 - 0.2077*PG3.1177*PG4 + 0.0341*PG5 + 0.5255*PG6 + 0.6014*PG7 + 0.2543*PG8$.

9. The computer-implemented method of claim 1, wherein said predetermined glycation equation is given by:

$$f(SMBG_t) = \text{MAX}\left(\gamma * \left(4.7561 + \frac{4.854}{1000} * mP_0(t) + CalA1c\right), 5\right)$$

where
- $mP_0(t)$ is the average fasting glucose over a predetermined period of time and is updated every time a new fasting glucose measurement is obtained from said patient,
- CalA1c is a calibration offset, and
- $\gamma$ is a glycation efficacy parameter;

the initial estimate of HbA1c is given by $eA1c(t_0) = f(SMBG_{t_0})$; and the updated estimate of HbA1c is given by $eA1c(t) = 0.95 * eA1c(t-1 \text{ day}) + 0.05 * f(SMBG_t)$.

10. A system for providing a real-time estimate of glycosylated hemoglobin (HbA1c) of a patient from a self-monitoring blood glucose (SMBG) measurement, and tracking changes in average glycemia of said patient over time, comprising:
- a processor; and
- a processor-readable memory including processor-executable instructions for:
  - receiving a fasting SMBG measurement from said patient;
  - computing a glycation value using said fasting SMBG measurement in a predetermined glycation equation;
  - outputting said glycation value as an initial estimate of HbA1c upon initialization of tracking of said patient's average glycemia;
  - updating said glycation value by using an updated SMBG value in said predetermined glycation equation, said updated SMBG value being based on a subsequent fasting SMBG measurement from said patient;
  - computing an updated estimate of HbA1c using said initial estimate of HbA1c and said updated glycation value in a predetermined HbA1c estimation equation; and
  - outputting said updated estimate of HbA1c to a user.

11. The system of claim 10, wherein said memory further includes processor-executable instructions for:
updating said updated estimate of HbA1c by:
using a subsequent updated SMBG value in said predetermined glycation equation based on a further subsequent fasting SMBG measurement from said patient to compute a further updated glycation value; and
computing a further updated estimate of HbA1c using a last updated estimate of HbA1c and said further updated glycation value in a predetermined HbA1c estimation equation; and
outputting said further updated estimate of HbA1c to a user.

12. The system of claim 11, wherein said predetermined glycation equation is given by:

$$f(SMBG_t) = \text{MAX}\left(\gamma * \left(4.7561 + \frac{4.854}{1000} * mP_0(t) + CalA1c\right), 5\right)$$

where
$mP_0(t)$ is the average fasting glucose over a predetermined period of time and is updated every time a new fasting glucose measurement is obtained from said patient,
CalA1c is a calibration offset, and
$\gamma$ is a glycation efficacy parameter;
the initial estimate of HbA1c is given by $eA1c(t_0)=f(SMBG_{t_0})$; and the updated estimate of HbA1c is given by $eA1c(t)=0.95*eA1c(t-1 \text{ day})+0.05*f(SMBG_t)$.

13. The system of claim 12, wherein $\gamma$ is set so that the last updated estimate of HbA1c, eA1c(t), is set to correspond to a reference HbA1c measurement obtained from said patient.

14. The system of claim 12, wherein $$CalA1c = \frac{6.507}{1000} * \theta_1 + \frac{4.353}{1000} * \theta_2,$$

$\theta_1$ and $\theta_2$ are predefined factors in a SMBG profile of said patient.

15. The system of claim 14, wherein said SMBG profile is a multipoint peri-prandial profile.

16. The system of claim 15, wherein said multipoint peri-prandial profile is a seven point profile including the following SMBG measurements:
PG2: first meal preprandial
PG3: first meal postprandial
PG4: second meal preprandial
PG5: second meal postprandial
PG6: third meal preprandial
PG7: third meal postprandial
PG8: before bedtime.

17. The system of claim 16, wherein $\theta_1$=0.4006*PG2+0.4645*PG3+0.3753*PG4+ 0.2411*PG5−0.1805*PG6−0.2528*PG7+ 0.0481*PG8, and $\theta_2$=−0.1557*PG2−0.2077*PG3.1177*PG4+ 0.0341*PG5+0.5255*PG6+0.6014*PG7+ 0.2543*PG8.

18. The system of claim 10, wherein said predetermined glycation equation is given by:

$$f(SMBG_t) = \text{MAX}\left(\gamma * \left(4.7561 + \frac{4.854}{1000} * mP_0(t) + CalA1c\right), 5\right)$$

where
$mP_0(t)$ is the average fasting glucose over a predetermined period of time and is updated every time a new fasting glucose measurement is obtained from said patient,
CalA1c is a calibration offset, and
$\gamma$ is a glycation efficacy parameter;
the initial estimate of HbA1c is given by $eA1c(t_0)=f(SMBG_{t_0})$; and the updated estimate of HbA1c is given by $eA1c(t)=0.95*eA1c(t-1 \text{ day})+0.05*f(SMBG_t)$.

19. A non-transient computer-readable medium having stored therein computer-executable instructions for providing a real-time estimate of glycosylated hemoglobin (HbA1c) of a patient from a self-monitoring blood glucose (SMBG) measurement, and tracking changes in average glycemia of said patient over time, said instructions comprising instructions causing a computer to:
receive a fasting SMBG measurement from said patient;
compute a glycation value using said fasting SMBG measurement in a predetermined glycation equation;
output said glycation value as an initial estimate of HbA1c upon initialization of tracking of said patient's average glycemia;
update said glycation value by using an updated SMBG value in said predetermined glycation equation, said updated SMBG value being based on a subsequent fasting SMBG measurement from said patient;
compute an updated estimate of HbA1c using said initial estimate of HbA1c and said updated glycation value in a predetermined HbA1c estimation equation; and
output said updated estimate of HbA1c to a user.

20. The computer-readable medium of claim 19, further including instructions for causing a computer to:
update said updated estimate of HbA1c by:
using a subsequent updated SMBG value in said predetermined glycation equation based on a further subsequent fasting SMBG measurement from said patient to compute a further updated glycation value; and
computing a further updated estimate of HbA1c using a last updated estimate of HbA1c and said further updated glycation value in a predetermined HbA1c estimation equation; and
output said further updated estimate of HbA1c to a user.

21. The computer-readable medium of claim 20, wherein said predetermined glycation equation is given by:

$$f(SMBG_t) = \text{MAX}\left(\gamma * \left(4.7561 + \frac{4.854}{1000} * mP_0(t) + CalA1c\right), 5\right)$$

where
$mP_0(t)$ is the average fasting glucose over a predetermined period of time and is updated every time a new fasting glucose measurement is obtained from said patient, CalAlc is a calibration offset, and
γ is a glycation efficacy parameter;
the initial estimate of HbA1c is given by $eA1c(t_0) = f(SMBG_{t_0})$; and the updated estimate of HbA1c is given by $eA1c(t) = 0.95*eA1c(t-1 \text{ day}) + 0.05*f(SMBG_t)$.

22. The computer-readable medium of claim 21, wherein γ is set so that the last updated estimate of HbA1c, eA1c(t), is set to correspond to a reference HbA1c measurement obtained from said patient.

23. The computer-readable medium of claim 21, wherein $$CalA1c = \frac{6.507}{1000}*\theta_1 + \frac{4.353}{1000}*\theta_2,$$

$\theta_1$ and $\theta_2$ are predefined factors in a SMBG profile of said patient.

24. The computer-readable medium of claim 23, wherein $\theta_1 = 0.4006*PG2 + 0.4645*PG3 + 0.3753*PG4 + 0.2411*PG5 - 0.1805*PG6 - 0.2528*PG7 + 0.0481*PG8$, and $\theta_2 = -0.1557*PG2 - 0.2077*PG3.1177*PG4 + 0.0341*PG5 + 0.5255*PG6 + 0.6014*PG7 + 0.2543*PG8$.

25. The computer-readable medium of claim 19, wherein said predetermined glycation equation is given by:

$$f(SMBG_t) = \text{MAX}\left(\gamma*\left(4.7561 + \frac{4.854}{1000}*mP_0(t) + CalA1c\right), 5\right)$$

where
mP$_0$(t) is the average fasting glucose over a predetermined period of time and is updated every time a new fasting glucose measurement is obtained from said patient,
CalA1c is a calibration offset, and
γ is a glycation efficacy parameter;
the initial estimate of HbA1c is given by $eA1c(t_0) = f(SMBG_{t_0})$; and the updated estimate of HbA1c is given by $eA1c(t) = 0.95*eA1c(t-1 \text{ day}) + 0.05*f(SMBG_t)$.

* * * * *